US012746392B2

(12) United States Patent
Parker et al.

(10) Patent No.: US 12,746,392 B2
(45) Date of Patent: Sep. 29, 2026

(54) PROGRAMMING OF NEUROSTIMULATION THERAPY

(71) Applicant: Saluda Medical Pty Ltd, Macquarie Park (AU)

(72) Inventors: John Louis Parker, Macquarie Park (AU); Dean Michael Karantonis, Macquarie Park (AU); Matthew Marlon Williams, Macquarie Park (AU); Samuel Nicholas Gilbert, Macquarie Park (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 444 days.

(21) Appl. No.: 18/356,975

(22) Filed: Jul. 21, 2023

(65) Prior Publication Data

US 2024/0024683 A1 Jan. 25, 2024

(30) Foreign Application Priority Data

Jul. 23, 2022 (AU) ................................ 2022902068

(51) Int. Cl.
*A61N 1/36* (2006.01)

(52) U.S. Cl.
CPC ..... *A61N 1/36132* (2013.01); *A61N 1/36146* (2013.01)

(58) Field of Classification Search
CPC ............ A61N 1/36132; A61N 1/36146; A61N 1/36062; A61N 1/36071; A61N 1/36139;
(Continued)

(56) References Cited

U.S. PATENT DOCUMENTS

| | | | |
|---|---|---|---|
| 8,812,125 | B2 | 8/2014 | Kaula et al. |
| 8,909,350 | B2 | 12/2014 | Lee |

(Continued)

FOREIGN PATENT DOCUMENTS

| | | |
|---|---|---|
| DE | 1020150 | 9/2016 |
| DE | 102015002565 | 9/2016 |

(Continued)

OTHER PUBLICATIONS

Gilbert, Samuel, “Virtual Reality for Pain Management: Evidence for Clinical Effectiveness and Strategies to Improve Outcomes”, S J Neurol Disord & Therapy, 2017, 1-2, pp. 1-13.

*Primary Examiner* — Mallika D Fairchild
(74) *Attorney, Agent, or Firm* — Barnes & Thornburg LLP

(57) ABSTRACT

Disclosed is a neurostimulation system comprising: a neuromodulation device for controllably delivering neural stimuli; a headset configured to be worn by the patient and to display images of a virtual object to the patient; one or more sensors configured to perceive a gesture of the patient; and an external computing device. The neuromodulation device comprises: a plurality of implantable electrodes; a stimulus source configured to deliver neural stimuli via selected ones of the implantable electrodes to a neural pathway of a patient; and a control unit configured to control the stimulus source to deliver each neural stimulus according to one or more stimulus parameters. The external computing device comprises a processor in communication with the neuromodulation device, the headset, and the one or more sensors. The processor is configured to: instruct the control unit to control the stimulus source to deliver neural stimuli according to the one or more stimulus parameters; render a virtual object to images for display to the patient via the headset; receive information indicative of a gesture of the patient from the sensors; and convert the gesture to a
(Continued)

manipulation of the virtual object. A posture of the patient may be detected and posture-dependent patient characteristics may be associated with the currently detected posture. The VR/AR environment may prompt the patient to assume a posture, so that currently estimated patient characteristics that are posture-dependent may be associated with the currently prompted posture.

6 Claims, 17 Drawing Sheets

(58) Field of Classification Search
CPC . A61N 1/37247; A61N 1/36185; G16H 40/63
See application file for complete search history.

(56) References Cited

U.S. PATENT DOCUMENTS

| | | | |
|---|---|---|---|
| 9,067,074 B2 | 6/2015 | Polefko et al. | |
| 9,174,055 B2 | 11/2015 | Davis et al. | |
| 10,376,701 B2 | 8/2019 | Kaula et al. | |
| 11,260,232 B2 | 3/2022 | Kaula et al. | |
| 11,298,550 B2 | 4/2022 | Howard et al. | |
| 2020/0016408 A1 | 1/2020 | Perryman et al. | |
| 2020/0030035 A1* | 1/2020 | Annoni | A61B 5/4848 |
| 2020/0046980 A1 | 2/2020 | Moffitt et al. | |
| 2020/0147388 A1 | 5/2020 | Huertas et al. | |
| 2021/0121702 A1 | 4/2021 | Lee | |
| 2022/0079501 A1 | 3/2022 | Zottola et al. | |
| 2022/0118260 A1 | 4/2022 | Zhu | |
| 2022/0134119 A1 | 5/2022 | McDonald et al. | |
| 2022/0152395 A1 | 5/2022 | Moffitt et al. | |
| 2022/0212014 A1 | 7/2022 | Steinke | |
| 2023/0060761 A1 | 3/2023 | Doan | |
| 2023/0149723 A1 | 5/2023 | Schmeling et al. | |
| 2023/0158291 A1 | 5/2023 | Steinke | |

FOREIGN PATENT DOCUMENTS

| | | |
|---|---|---|
| WO | WO2007030635 A1 | 3/2007 |
| WO | WO2007097858 A1 | 8/2007 |
| WO | WO2007097859 A1 | 8/2007 |
| WO | WO2007097861 A1 | 8/2007 |
| WO | WO2007100427 A1 | 9/2007 |
| WO | WO2007102945 A2 | 9/2007 |
| WO | WO2008070140 A2 | 6/2008 |
| WO | WO2009079600 A3 | 8/2009 |
| WO | WO2011085228 A1 | 7/2011 |
| WO | WO2012057951 A1 | 5/2012 |
| WO | WO2012061206 A1 | 5/2012 |
| WO | WO2012/155183 | 11/2012 |
| WO | WO2012155188 A1 | 11/2012 |
| WO | WO2012158830 A1 | 11/2012 |
| WO | WO2012158882 A1 | 11/2012 |
| WO | WO2013152124 A1 | 10/2013 |
| WO | WO2014058650 A1 | 4/2014 |
| WO | WO2014150001 A1 | 9/2014 |
| WO | WO2014036079 A3 | 10/2014 |
| WO | WO2014145222 A3 | 12/2014 |
| WO | WO2015/074121 | 5/2015 |
| WO | WO2016044169 A1 | 3/2016 |
| WO | WO2016172239 A1 | 10/2016 |
| WO | WO2017019191 A1 | 2/2017 |
| WO | WO2017048963 A1 | 3/2017 |
| WO | WO2017066187 A1 | 4/2017 |
| WO | WO2017160442 A1 | 9/2017 |
| WO | WO2018063879 A1 | 4/2018 |
| WO | WO2018097918 A1 | 5/2018 |
| WO | WO2018182881 A1 | 10/2018 |
| WO | WO2018187090 A1 | 10/2018 |
| WO | WO2019036180 A1 | 2/2019 |
| WO | WO2019210214 A1 | 10/2019 |
| WO | WO2019231794 A1 | 12/2019 |
| WO | WO2020005589 A1 | 1/2020 |
| WO | WO2020010120 A1 | 1/2020 |
| WO | WO2020068433 A1 | 4/2020 |
| WO | WO2020162990 A2 | 8/2020 |
| WO | WO2020257301 A1 | 12/2020 |
| WO | WO2021194684 A1 | 9/2021 |
| WO | WO2023028435 A1 | 3/2023 |
| WO | WO2023102557 A1 | 6/2023 |
| WO | WO2023115132 A1 | 6/2023 |
| WO | WO2023115145 A1 | 6/2023 |
| WO | WO2023/205858 | 11/2023 |

* cited by examiner

PROGRAMMING OF NEUROSTIMULATION THERAPY

The present application claims priority from Australian Provisional Patent Application No. 2022902068 filed on Jul. 23, 2022, the contents of which are incorporated herein by reference in their entirety.

TECHNICAL FIELD

The present invention relates to neural stimulation therapy and in particular to systems and methods for improved programming of neural stimulation therapy assisted by virtual reality/augmented reality devices.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation device applies an electrical pulse (stimulus) to neural tissue (fibres, or neurons) in order to generate a therapeutic effect. In general, the electrical stimulus generated by a neuromodulation device evokes a neural response known as an action potential in a neural fibre which then has either an inhibitory or excitatory effect. Inhibitory effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a device typically comprises an implanted electrical pulse generator, and a power source such as a battery that may be transcutaneously rechargeable by wireless means, such as inductive transfer. An electrode array is connected to the pulse generator, and is implanted adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates an action potential in the fibres. Action potentials propagate along the fibres in orthodromic (in afferent fibres this means towards the head, or rostral) and antidromic (in afferent fibres this means towards the cauda, or caudal) directions. Action potentials propagating along Aβ (A-beta) fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

For effective and comfortable neuromodulation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it is therefore desirable to apply stimuli with intensity below a discomfort threshold, above which uncomfortable or painful percepts arise due to over-recruitment of Aβ fibres. When recruitment is too large, Aβ fibres produce uncomfortable sensations. Stimulation at high intensity may even recruit Aδ (A-delta) fibres, which are sensory nerve fibres associated with acute pain, cold and heat sensation. It is therefore desirable to maintain stimulus intensity within a therapeutic range between the recruitment threshold and the discomfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Attempts have been made to address such problems by way of feedback or closed-loop control, such as using the methods set forth in International Patent Publication No. WO2012/155188 by the present applicant. Feedback control seeks to compensate for relative nerve/electrode movement by controlling the intensity of the delivered stimuli so as to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range.

It is therefore desirable to accurately measure the intensity and other characteristics of a neural response evoked by the stimulus. The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO2012/155183, the content of which is incorporated herein by reference.

Closed-loop neural stimulation therapy is governed by a number of parameters to which values must be assigned to implement the therapy. The effectiveness of the therapy depends in large measure on the suitability of the assigned parameter values to the patient undergoing the therapy. As patients vary significantly in their physiological characteristics, a "one-size-fits-all" approach to parameter value assignment is likely to result in ineffective therapy for a large proportion of patients. An important preliminary task, once a neuromodulation device has been implanted in a patient, is therefore to assign values to the therapy parameters that maximise the effectiveness of the therapy the device will deliver to that particular patient. This task is known as programming or fitting the device. Programming generally involves applying certain test stimuli via the device, recording responses, and based on the recorded responses, inferring or calculating the most effective parameter values for the patient. The resulting parameter values are then formed into a "program" that may be loaded to the device to govern subsequent therapy. Some of the recorded responses may be neural responses evoked by the test stimuli, which provide an objective source of information that may be analysed. Obtaining patient feedback about their sensations in response to the test stimuli is also important during programming of closed-loop neural stimulation therapy. However, mediation between patients and the programming system by trained clinical engineers is expensive and time-consuming.

Moreover, thresholds for discomfort vary widely between patients, between postures for a single patient, and between stimulus electrodes for a given patient in a given posture. It is difficult to know in advance where a given patient's discomfort threshold is in a given posture. The result is that a test stimulus of an intensity that is comfortable for one patient may provoke acute discomfort for another patient, or for the same patient in a different posture, or for the same patient in the same posture when applied at a different stimulus electrode. This complicates certain aspects of programming involving measurement of the intensity of patients' neural responses across the full comfortable range of stimulus intensity at a particular stimulus electrode.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

Disclosed herein is a programming system for a neuromodulation device that is assisted by virtual reality (VR)/augmented reality (AR) functionality. The VR/AR-assisted programming system renders virtual objects to the field of view of the patient wearing a VR/AR headset. The patient may interact with the virtual objects to either control and adjust parameters of test stimuli being delivered in real time, or provide feedback about the sensations they are experiencing either before or as a result of the test stimuli being delivered. Alternatively, or additionally, a posture sensor forming part of the VR/AR equipment may detect a (static or dynamic) posture of the patient, so that currently estimated patient characteristics that are posture-dependent may be associated with the currently detected posture. Alternatively, or additionally, the VR/AR environment may prompt the patient to assume a posture, so that currently estimated patient characteristics that are posture-dependent may be associated with the currently prompted posture.

According to a first aspect of the present technology, there is provided a neurostimulation system comprising: a neuromodulation device for controllably delivering neural stimuli; a headset configured to be worn by the patient and to display images of a virtual object to the patient; one or more sensors configured to perceive a gesture of the patient; and an external computing device. The neuromodulation device comprises: a plurality of implantable electrodes; a stimulus source configured to deliver neural stimuli via one or more of the implantable electrodes to a neural pathway of a patient; and a control unit configured to control the stimulus source to deliver each neural stimulus according to one or more stimulus parameters. The external computing device comprises a processor in communication with the neuromodulation device, the headset, and the one or more sensors. The processor is configured to: instruct the control unit to control the stimulus source to deliver a neural stimulus according to the one or more stimulus parameters; transmit the virtual object to the headset for display to the patient; receive information indicative of a gesture of the patient from the one or more sensors; and convert the information indicative of the gesture to a manipulation of the virtual object.

According to a second aspect of the present technology, there is provided an automated method of controllably delivering a neural stimulus to a patient. The method comprises: delivering neural stimuli to a patient according to one or more stimulus parameters; rendering a virtual object to images for display to the patient via a headset configured to be worn by the patient and to display images of a virtual object to the patient; receiving information indicative of a gesture of the patient via one or more sensors configured to perceive a gesture of the patient; and converting the information indicative of the gesture to a manipulation of the virtual object.

According to a third aspect of the present technology, there is provided a neurostimulation system comprising a neuromodulation device for controllably delivering neural stimuli; a posture sensor configured to detect a posture of the patient; and an external computing device. The neuromodulation device comprises: a plurality of implantable electrodes; a stimulus source configured to deliver neural stimuli via one or more of the implantable electrodes to a neural pathway of a patient; and a control unit configured to control the stimulus source to deliver each neural stimulus according to one or more stimulus parameters. The external computing device comprises a processor in communication with the neuromodulation device and the posture sensor. The processor is configured to: instruct the control unit to control the stimulus source to deliver a neural stimulus according to the one or more stimulus parameters; receive information indicative of a detected posture of the patient from the posture sensor; and store data related to the neural stimuli in association with the information indicative of the detected posture.

According to a fourth aspect of the present technology, there is provided an automated method of controllably delivering a neural stimulus to a patient. The method comprises: delivering neural stimuli to a patient according to one or more stimulus parameters; receiving information indicative of a detected posture of the patient from a posture sensor configured to detect a posture of the patient; and storing data related to the neural stimuli in association with the information indicative of the detected posture.

According to a fifth aspect of the present technology, there is provided a neurostimulation system comprising: a neuromodulation device for controllably delivering neural stimuli; a headset configured to be worn by the patient and to display a virtual object to the patient; and an external computing device. The neuromodulation device comprises: a plurality of implantable electrodes; a stimulus source configured to deliver neural stimuli via one or more of the implantable electrodes to a neural pathway of a patient; and a control unit configured to control the stimulus source to deliver each neural stimulus according to one or more stimulus parameters. The external computing device comprises a processor in communication with the neuromodulation device and the headset. The processor is configured to: instruct the control unit to control the stimulus source to deliver a neural stimulus according to the one or more stimulus parameters; transmit the virtual object to the headset, the virtual object configured to prompt the patient to assume a first posture; and store data related to the neural stimuli in association with the first posture.

According to a sixth aspect of the present technology, there is provided an automated method of controllably delivering neural stimuli to a patient. The method comprises: delivering neural stimuli according to one or more stimulus parameters; rendering a virtual object to images for display to the patient via a headset so as to prompt the patient to assume a first posture, the headset being configured to be worn by the patient and to display images of a virtual object to the patient; and storing data related to the neural stimuli in association with the first posture.

References herein to estimation, determination, comparison and the like are to be understood as referring to an automated process carried out on data by a processor operating to execute a predefined procedure suitable to effect the described estimation, determination and/or comparison step (s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which.

DETAILED DESCRIPTION OF THE PRESENT TECHNOLOGY

Figure 1:
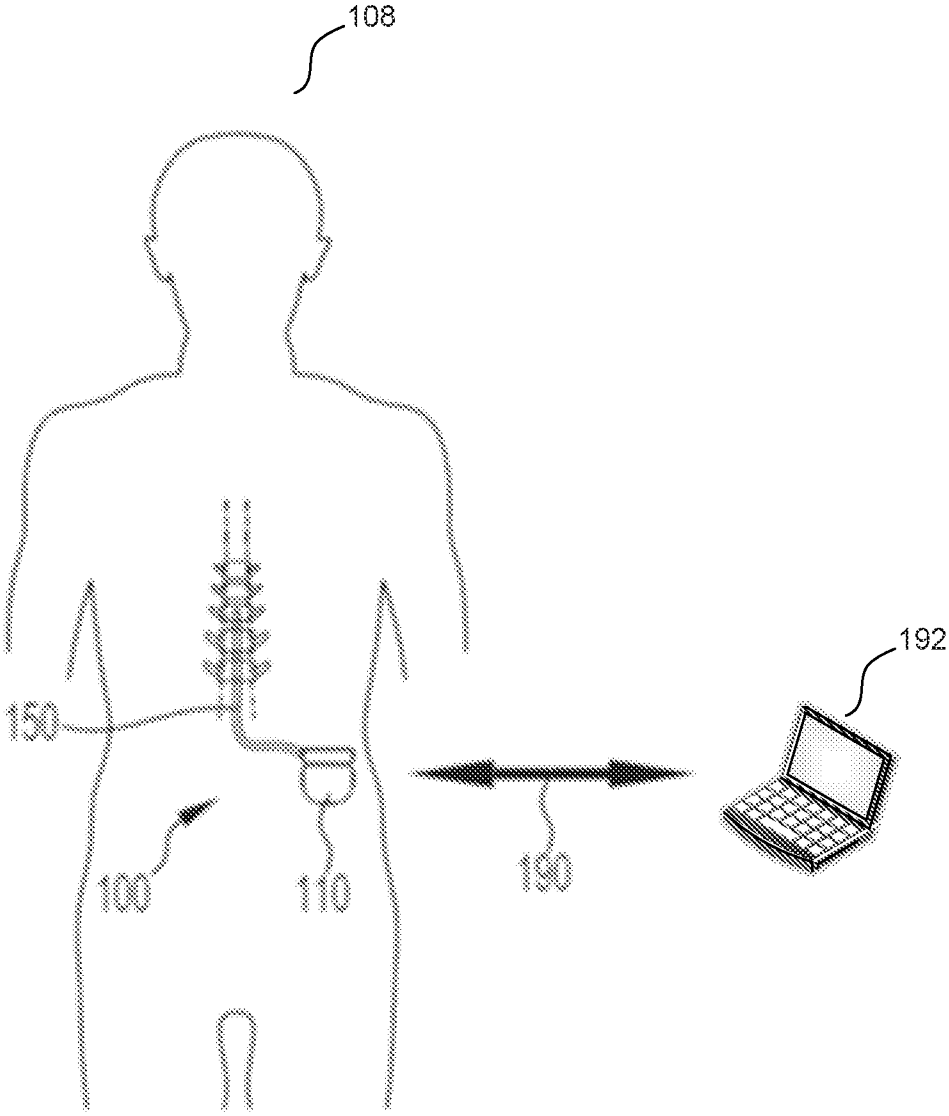
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as in a flank or sub-clavicularly. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. External device 192 may thus provide a clinical interface configured to program the implanted stimulator 100 and recover data stored on the implanted stimulator 100. This configuration is achieved by program instructions collectively referred to as the Clinical Programming Application (CPA) and stored in an instruction memory of the clinical interface.

Figure 2:
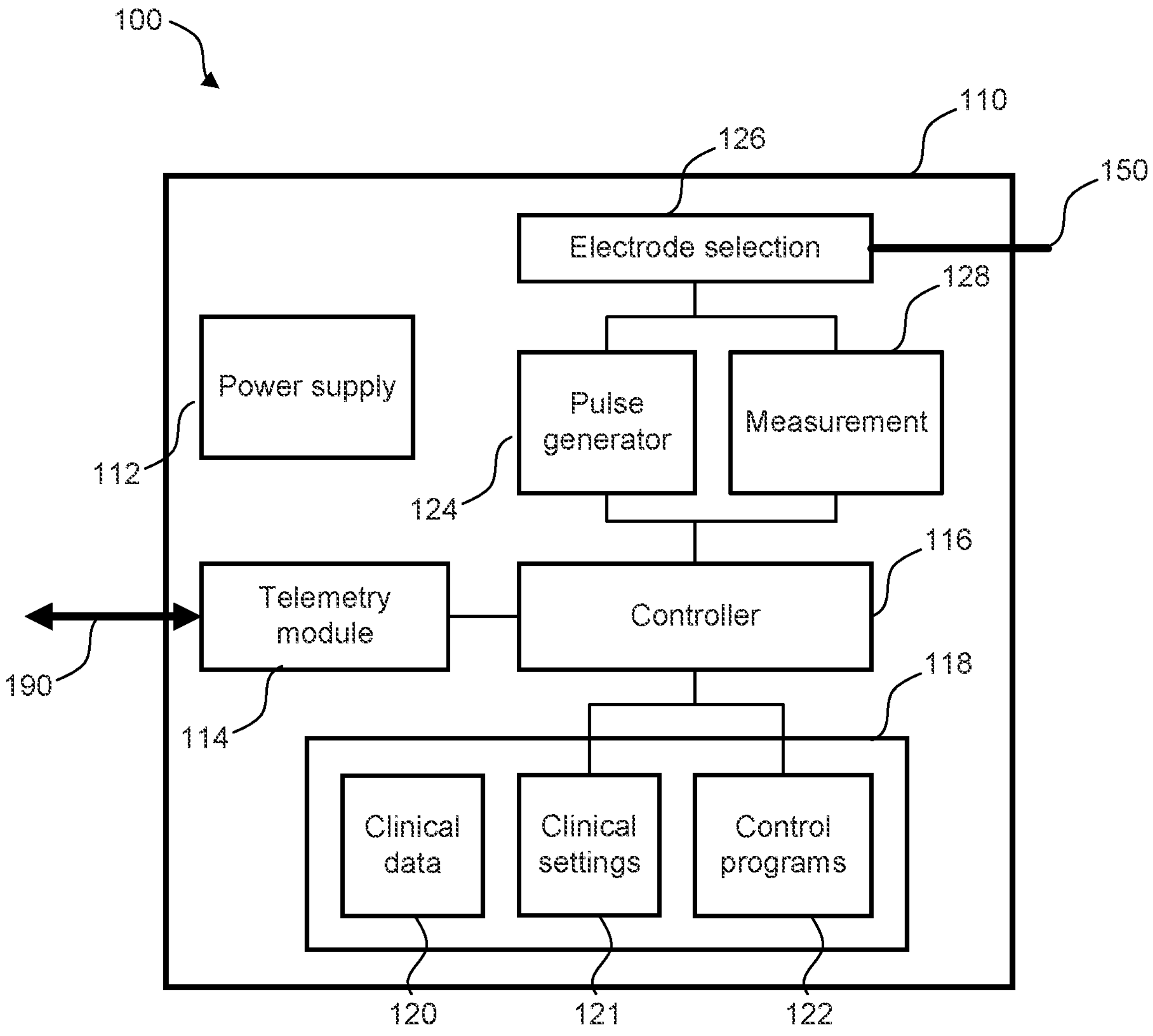
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communications channel 190, such as infrared (IR), radiofrequency (RF), capacitive and/or inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 is configured by control programs 122, sometimes referred to as firmware, to control a pulse generator 124 to generate stimuli, such as in the form of electrical pulses, in accordance with the clinical settings 121. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process signals comprising neural responses sensed at measurement electrode(s) of the electrode array 150 as selected by electrode selection module 126.

Figure 3:
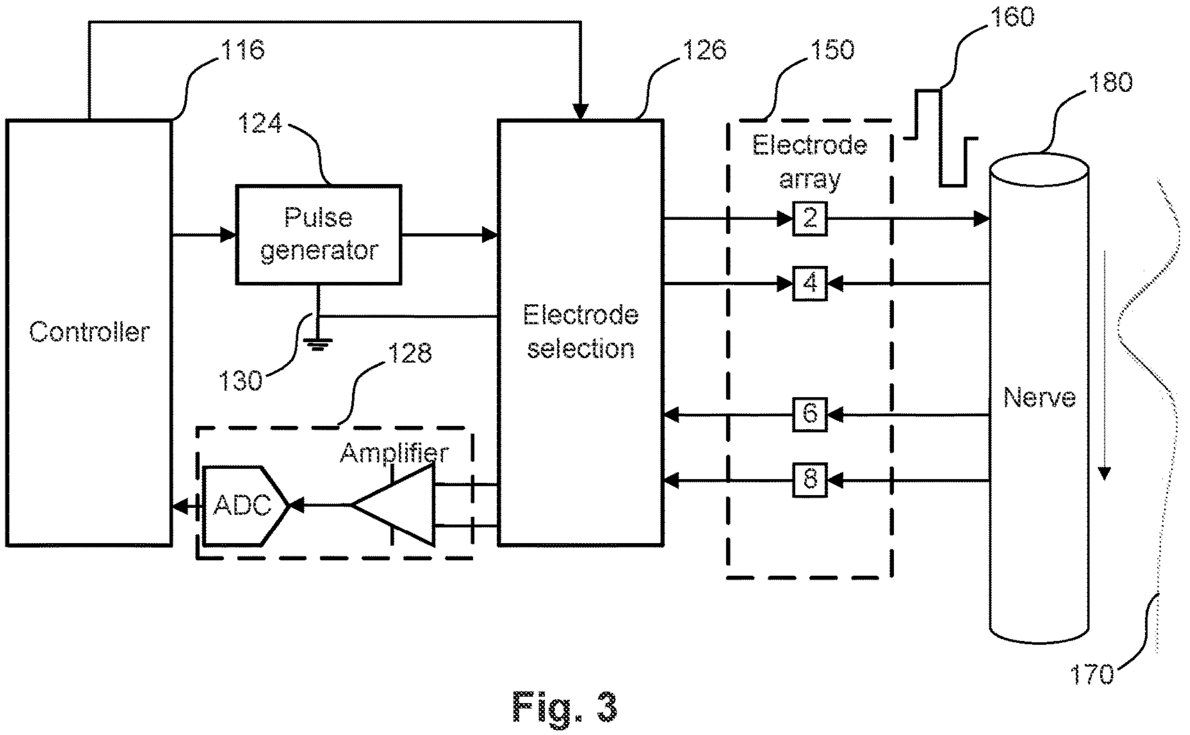
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g. a biphasic stimulus pulse 160 comprises two phases. Electrode selection module 126 also selects a return electrode 4 of the electrode array 150 for stimulus current return in each phase, to maintain a zero net charge transfer. An electrode may act as both a stimulus and a return electrode over a complete multiphasic stimulus pulse. The use of two electrodes in this manner for delivering and returning current in each stimulus phase is referred to as bipolar stimulation. Alternative embodiments may apply other forms of bipolar stimulation, or may use a greater number of stimulus and/or return electrodes. The set of stimulus and return electrodes and their respective polarities is referred to as the stimulus electrode configuration (SEC). Electrode selection module 126 is illustrated as connecting to a ground 130 of the pulse generator 124 to enable stimulus current return via the return electrode 4. However, other connections for charge recovery may be used in other implementations.

Delivery of an appropriate stimulus via stimulus electrodes 2 and 4 to the nerve 180 evokes a neural response 170 comprising an evoked compound action potential (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To program the stimulator 100 to the patient 108, a clinician may cause the stimulator 100 to deliver stimuli of various configurations which seek to produce a sensation that is experienced by the user as paraesthesia. When a stimulus electrode configuration is found which evokes paraesthesia in a location and of a size which is congruent with the area of the patient's body affected by pain and of a quality that is comfortable for the patient, the clinician or the patient nominates that configuration for ongoing use. The program parameters may be loaded into the memory 118 of the stimulator 100 as the clinical settings 121.

Figure 6:
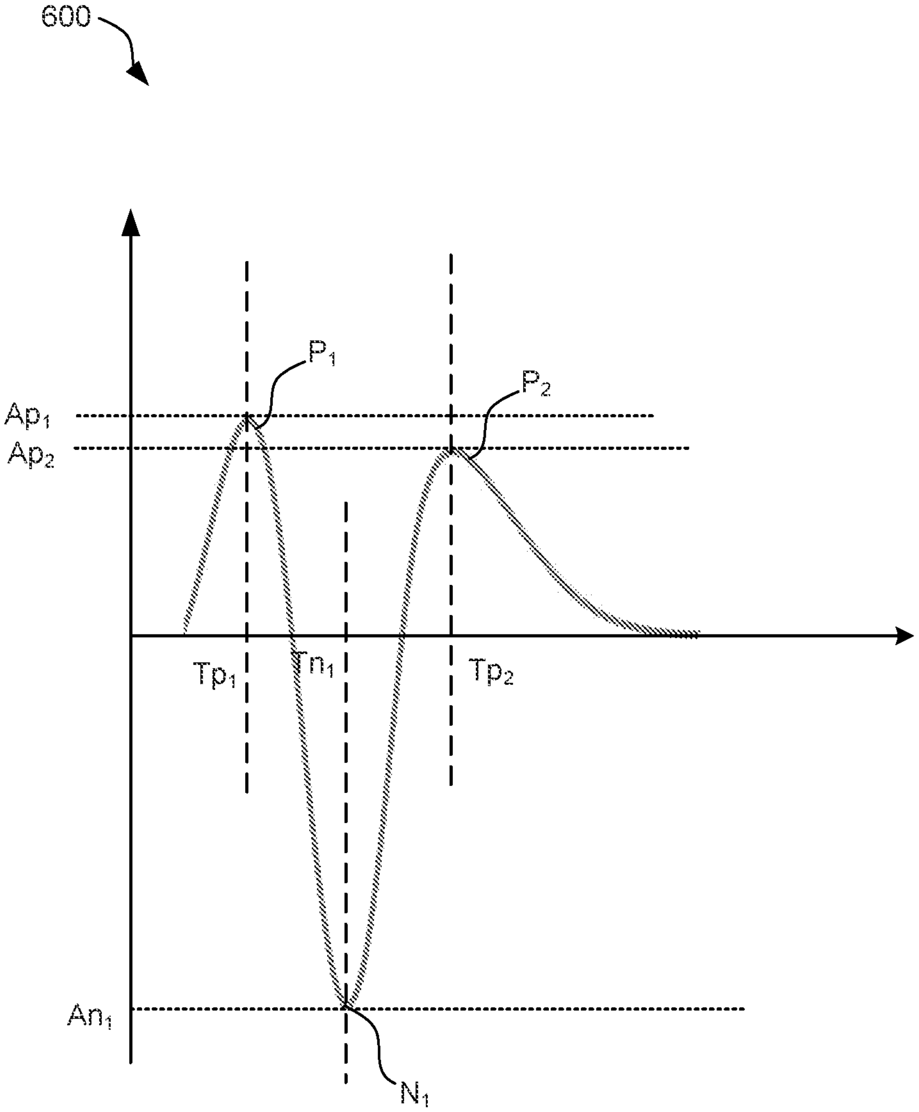
FIG. 6 illustrates the typical form of an electrically evoked compound action potential (ECAP) of a healthy subject.

FIG. 6 illustrates the typical form of an ECAP 600 of a healthy subject, as recorded at a single measurement electrode referenced to the system ground 130. The shape and duration of the single-ended ECAP 600 shown in FIG. 6 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Differential ECAP measurements are less subject to common-mode noise on the surrounding tissue than single-ended ECAP measurements. Depending on the polarity of recording, a differential ECAP may take an inverse form to that shown in FIG. 6, i.e. a form having two negative peaks N1 and N2, and one positive peak P1. Alternatively, depending on the distance between the two measurement electrodes, a differential ECAP may resemble the time derivative of the ECAP 600, or more generally the difference between the ECAP 600 and a time-delayed copy thereof.

The ECAP 600 may be characterised by any suitable characteristic(s) of which some are indicated in FIG. 6. The amplitude of the positive peak P1 is $Ap_1$ and occurs at time $Tp_1$. The amplitude of the positive peak P2 is Ape and occurs at time $Tp_2$. The amplitude of the negative peak P1 is $An_1$ and occurs at time $Tn_1$. The peak-to-peak amplitude is $Ap_1+An_1$. A recorded ECAP will typically have a maximum peak-to-peak amplitude in the range of microvolts and a duration of 2 to 3 ms.

Returning to FIG. 3, the stimulator 100 is further configured to detect the existence and measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and reference electrode 8, whereby the electrode selection module 126 selectively connects the chosen electrodes to the inputs of the measurement circuitry 128. Thus, signals sensed by the measurement electrodes 6 and 8 subsequent to the respective stimuli are passed to the measurement circuitry 128, which may comprise a differential amplifier and an analog-to-digital converter (ADC), as illustrated in FIG. 3. The recording electrode and the reference electrode are referred to as the measurement electrode configuration. The measurement circuitry 128 for example may operate in accordance with the teachings of the above-mentioned International Patent Publication No. WO2012/155183.

Signals sensed by the measurement electrodes 6, 8 and processed by measurement circuitry 128 are further processed by an ECAP detector implemented within controller 116, configured by control programs 122, to obtain information regarding the effect of the applied stimulus upon the nerve 180. In some implementations, the sensed signals are processed by the ECAP detector in a manner which measures and stores one or more characteristics from each evoked neural response or group of evoked neural responses contained in the sensed signal. In one such implementation, the characteristics comprise a peak-to-peak ECAP amplitude in microvolts (μV). For example, the sensed signals may be processed by the ECAP detector to determine the peak-to-peak ECAP amplitude in accordance with the teachings of International Patent Publication No. WO2015/074121, the contents of which are incorporated herein by reference. Alternative implementations of the ECAP detector may measure and store an alternative characteristic from the neural response, or may measure and store two or more characteristics from the neural response.

Stimulator 100 applies stimuli over a potentially long period such as days, weeks, or months and during this time may store characteristics of neural responses, clinical settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more characteristics such as a measure of the intensity of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

Figure 4A:
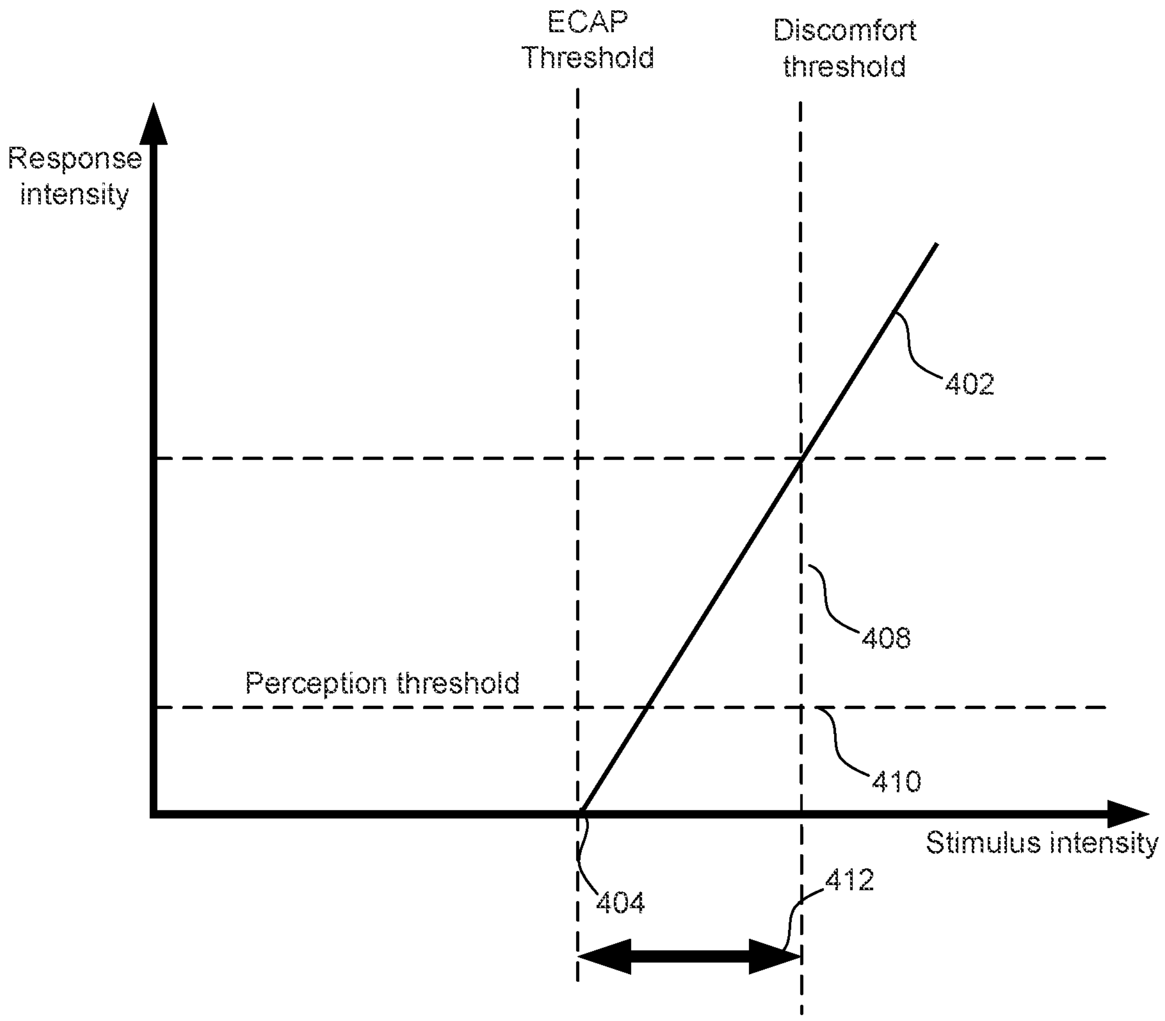
FIG. 4*a* illustrates an idealised activation plot for one posture of a patient undergoing neural stimulation.

An activation plot, or growth curve, is an approximation to the relationship between stimulus intensity (e.g. an amplitude of the current pulse 160) and intensity of neural response 170 evoked by the stimulus (e.g. an ECAP amplitude). FIG. 4*a* illustrates an idealised activation plot 402 for one posture of the patient 108. The activation plot 402 shows a linearly increasing ECAP amplitude for stimulus intensity values above a threshold 404 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 404 therefore reflects the field strength at which significant numbers of fibres begin to be recruited, and the increase in response intensity with stimulus intensity above the ECAP threshold reflects increasing numbers of fibres being recruited. Below the ECAP threshold 404, the ECAP amplitude may be taken to be zero. Above the ECAP threshold 404, the activation plot 402 has a positive, approximately constant slope indicating a linear relationship between stimulus intensity and the ECAP amplitude. Such a relationship may be modelled as:

$$y = \begin{cases} S(s-T), & s \geq T \\ 0, & s < T \end{cases} \tag{1}$$

where s is the stimulus intensity, y is the ECAP amplitude, T is the ECAP threshold and S is the slope of the activation plot (referred to herein as the patient sensitivity). The sensitivity S and the ECAP threshold T are the key parameters of the activation plot 402.

FIG. 4*a* also illustrates a discomfort threshold 408, which is a stimulus intensity above which the patient 108 experiences uncomfortable or painful stimulation. FIG. 4*a* also illustrates a perception threshold 410. The perception threshold 410 corresponds to an ECAP amplitude that is perceivable by the patient. There are a number of factors which can influence the position of the perception threshold 410, including the posture of the patient. Perception threshold 410 may correspond to a stimulus intensity that is greater than the ECAP threshold 404, as illustrated in FIG. 4*a*, if patient 108 does not perceive low levels of neural activation. Conversely, the perception threshold 410 may correspond to a stimulus intensity that is less than the ECAP threshold 404, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it is desirable to maintain stimulus intensity within a therapeutic range. A stimulus intensity within a therapeutic range 412 is above the ECAP threshold 404 and below the discomfort threshold 408. In principle, it would be straightforward to measure these limits and ensure that stimulus intensity, which may be closely controlled, always falls within the therapeutic range 412. However, the activation plot, and therefore the therapeutic range 412, varies with the posture of the patient 108.

Figure 4B:
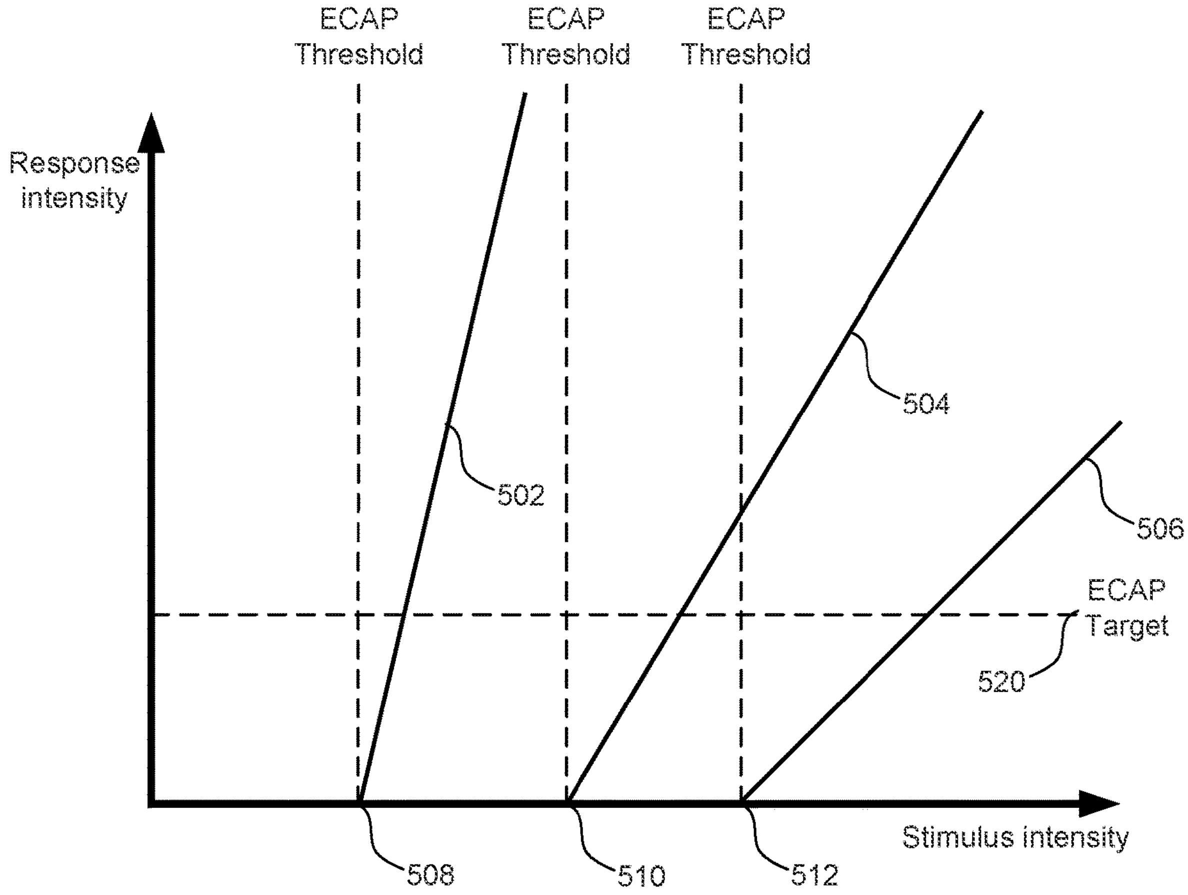
FIG. 4*b* illustrates the variation in the activation plots with changing posture of the patient.

FIG. 4*b* illustrates the variation in the activation plots with changing posture of the patient. A change in posture of the patient may cause a change in impedance of the electrode-tissue interface or a change in the distance between electrodes and the neurons. While the activation plots for only three postures, 502, 504 and 506, are shown in FIG. 4*b*, the activation plot for any given posture can lie between or outside the activation plots shown, on a continuously varying basis depending on posture. Consequently, as the patient's posture changes, the ECAP threshold changes, as indicated by the ECAP thresholds 508, 510, and 512 for the respective activation plots 502, 504, and 506. Additionally, as the patient's posture changes, the slope of the activation plot also changes, as indicated by the varying slopes of activation plots 502, 504, and 506. In general, as the distance between the stimulus electrodes and the spinal cord increases, the ECAP threshold increases and the slope of the activation plot decreases. The activation plots 502, 504, and 506 therefore correspond to increasing distance between stimulus electrodes and spinal cord, and decreasing patient sensitivity.

To keep the applied stimulus intensity within the therapeutic range as patient posture varies, in some implementations an implantable neuromodulation device such as the stimulator 100 may adjust the applied stimulus intensity based on a feedback variable that is determined from one or more measured ECAP characteristics. In one implementation, the device may adjust the stimulus intensity to maintain the measured ECAP amplitude at a target response intensity. For example, the device may calculate an error between a target ECAP amplitude and a measured ECAP amplitude, and adjust the applied stimulus intensity to reduce the error as much as possible, such as by adding the scaled error to the current stimulus intensity. A neuromodulation device that operates by adjusting the applied stimulus intensity based on a measured ECAP characteristic is said to be operating in closed-loop mode and will also be referred to as a closed-loop neural stimulation (CLNS) device. By adjusting the applied stimulus intensity to maintain the measured ECAP amplitude at an appropriate target response intensity, such as an ECAP target 520 illustrated in FIG. 4*b*, a CLNS device will generally keep the stimulus intensity within the therapeutic range as patient posture varies.

A CLNS device comprises a stimulator that takes a stimulus intensity value and converts it into a neural stimulus comprising a sequence of electrical pulses according to a predefined stimulation pattern. The stimulation pattern is parametrised by multiple stimulus parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The intensity of an evoked neural response (e.g. an ECAP) is detected, and its amplitude measured by the CLNS device and compared to the target response intensity.

The measured neural response intensity, and its deviation from the target response intensity, is used by the feedback loop to determine possible adjustments to the stimulus intensity parameter to maintain the neural response at the target intensity. If the target intensity is properly chosen, the patient receives consistently comfortable and therapeutic stimulation through posture changes and other perturbations to the stimulus/response behaviour.

Figure 5:
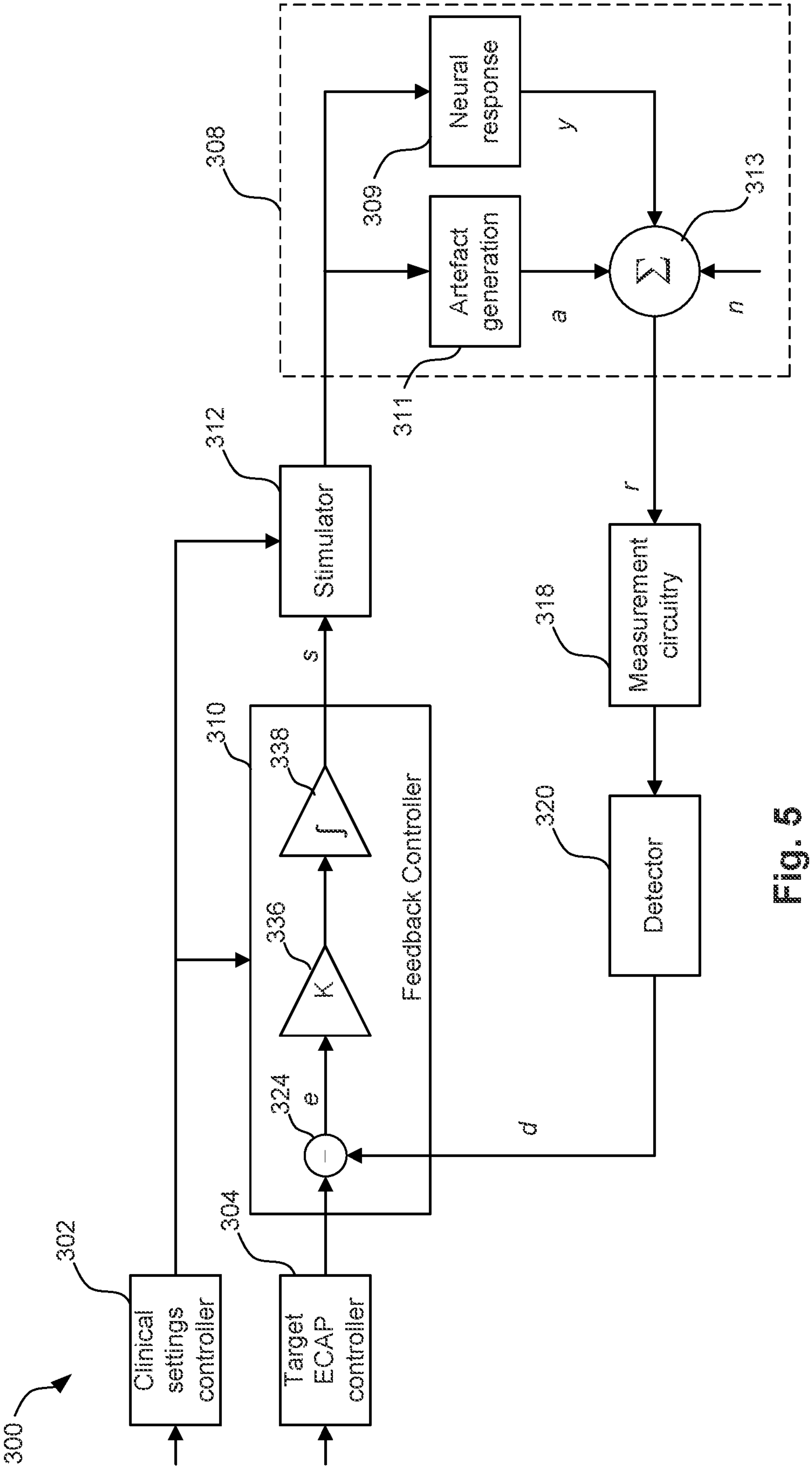
FIG. 5 is a schematic illustrating elements and inputs of a closed-loop neural stimulation (CLNS) system, according to one implementation of the present technology.

FIG. 5 is a schematic illustrating elements and inputs of a closed-loop neural stimulation (CLNS) system 300, according to one implementation of the present technology. The system 300 comprises a stimulator 312 which converts a stimulus intensity parameter (for example a stimulus current amplitude) s, in accordance with a set of predefined stimulus parameters, to a neural stimulus comprising a sequence of electrical pulses on the stimulus electrodes (not shown in FIG. 5). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. Various sources of measurement noise n, as well as the artefact a, may add to the evoked response y at the summing element 313 to form the sensed signal r, including: electrical noise from external sources such as 50 Hz mains power; electrical disturbances produced by the body such as neural responses evoked not by the device but by other causes such as peripheral sensory input; EEG; EMG; and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

Measurement circuitry 318, which may be identified with measurement circuitry 128, amplifies the sensed signal r (including evoked neural response, artefact, and measurement noise), and samples the amplified sensed signal r to capture a “signal window” comprising a predetermined number of samples of the amplified sensed signal r. The ECAP detector 320 processes the signal window and outputs a measured neural response intensity d. A typical number of samples in a captured signal window is 60. In one implementation, the neural response intensity comprises a peak-to-peak ECAP amplitude. The measured response intensity d is input into the feedback controller 310. The feedback controller 310 comprises a comparator 324 that compares the measured response intensity d to the target ECAP amplitude as set by the target ECAP controller 304 and provides an indication of the difference between the measured response intensity d and the target ECAP amplitude. This difference is the error value, e.

The feedback controller 310 calculates an adjusted stimulus intensity parameter, s, with the aim of maintaining a measured response intensity d equal to the target ECAP amplitude. Accordingly, the feedback controller 310 adjusts the stimulus intensity parameter s to minimise the error value, e. In one implementation, the controller 310 utilises a first order integrating function, using a gain element 336 and an integrator 338, in order to provide suitable adjustment to the stimulus intensity parameter s. According to such an implementation, the current stimulus intensity parameter s may be determined by the feedback controller 310 as $$s = \int K e dt \tag{2}$$

where K is the gain of the gain element 336 (the controller gain). This relation may also be represented as $$\delta s = Ke \tag{3}$$

where δs is an adjustment to the current stimulus intensity parameter s.

A target ECAP amplitude is input to the feedback controller 310 via the target ECAP controller 304. In one embodiment, the target ECAP controller 304 provides an indication of a specific target ECAP amplitude. In another embodiment, the target ECAP controller 304 provides an indication to increase or to decrease the present target ECAP amplitude. The target ECAP controller 304 may comprise an input into the CLNS system 300, via which the patient or clinician can input a target ECAP amplitude, or indication thereof. The target ECAP controller 304 may comprise memory in which the target ECAP amplitude is stored, and from which the target ECAP amplitude is provided to the feedback controller 310.

A clinical settings controller 302 provides clinical settings to the system 300, including the feedback controller 310 and the stimulus parameters for the stimulator 312 that are not under the control of the feedback controller 310. In one example, the clinical settings controller 302 may be configured to adjust the controller gain K of the feedback controller 310 to adapt the feedback loop to patient sensitivity. The clinical settings controller 302 may comprise an input into the CLNS system 300, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at a sampling frequency of 10 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus intensity is updated in light of the error value e.

Figure 7:
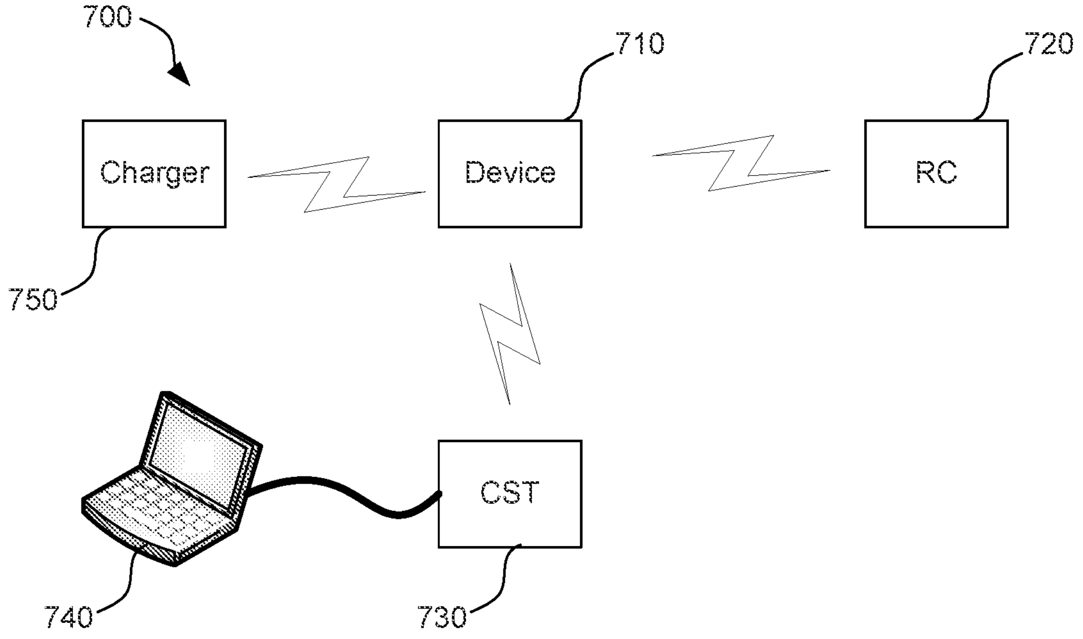
FIG. 7 is a block diagram of a neural stimulation therapy system including the implanted stimulator of FIG. 1 according to one implementation of the present technology.

FIG. 7 is a block diagram of a neural stimulation system 700. The neural stimulation system 700 is centred on a neuromodulation device 710. In one example, the neuromodulation device 710 may be implemented as the stimulator 100 of FIG. 1, implanted within a patient (not shown). The neuromodulation device 710 may in some implementations be a CLNS device. The neuromodulation device 710 is connected wirelessly to a remote controller (RC) 720. The remote controller 720 is a portable computing device that provides the patient with control of their stimulation in the home environment by allowing control of the functionality of the neuromodulation device 710, including one or more of the following functions: enabling or disabling stimulation; adjustment of stimulus intensity or target neural response intensity; and selection of a stimulation control program from the control programs stored on the neuromodulation device 710.

The charger 750 is configured to recharge a rechargeable power source of the neuromodulation device 710. The recharging is illustrated as wireless in FIG. 7 but may be wired in alternative implementations.

The neuromodulation device 710 is wirelessly connected to a Clinical System Transceiver (CST) 730. The wireless connection may be implemented as the transcutaneous communications channel 190 of FIG. 1. The CST 730 acts as an intermediary between the neuromodulation device 710 and the Clinical Interface (CI) 740, to which the CST 730 is connected. A wired connection is shown in FIG. 7, but in other implementations, the connection between the CST 730 and the CI 740 is wireless.

The CI 740 may be implemented as the external computing device 192 of FIG. 1. The CI 740 is configured to program the neuromodulation device 710 and recover data stored on the neuromodulation device 710. This configuration is achieved by program instructions collectively referred to as the Clinical Programming Application (CPA) and stored in an instruction memory of the CI 740.

The Assisted Programming System

As mentioned above, obtaining patient feedback about their sensations is important during programming of closed-loop neurostimulation, but mediation by trained clinical engineers is expensive and time-consuming. It would therefore be advantageous if patients could program their own implantable device themselves, or at least partly by themselves with reduced assistance from a clinician. However, interfaces for current programming systems are non-intuitive and generally unsuitable for direct use by patients because of their technical nature. There is therefore a need for a CPA to be as intuitive for non-technical users as possible while avoiding discomfort to the patient.

Implementations of an Assisted Programming System (APS) according to the present technology are generally configured to meet this need. In some implementations, the APS comprises two elements: the Assisted Programming Module (APM), which forms part of the CPA, and the Assisted Programming Firmware (APF), which forms part of the control programs 122 executed by the controller 116 of the electronics module 110. The data obtained from the patient is analysed by the APM to determine the parameters and settings for the neural stimulation therapy to be delivered by the stimulator 100. The APF is configured to complement the operation of the APM by responding to commands issued by the APM via the CST 730 to the stimulator 100 to deliver specified stimuli to the patient, and by returning, via the CST 730, measurements of neural responses to the delivered stimuli.

In other implementations, all the processing of the APS according to the present technology is done by the APF. In other words, the data obtained from the patient is not passed to the APM, but is analysed by the APF to determine the parameters and settings for the neural stimulation therapy to be delivered by the stimulator 100.

In implementations of the APS in which the APM analyses the data from the patient, the APS instructs the device 710 to capture and return signal windows to the CI 740 via the CST 730. In such implementations, the device 710 captures the signal windows using the measurement circuit 128 and bypasses the ECAP detector 320, storing the data representing the raw signal windows temporarily in memory 118 before transmitting the data representing the captured signal windows to the APS for analysis.

Following the programming, the APS may load the determined program onto the device 710 to govern subsequent neurostimulation therapy. In one implementation, the program comprises clinical settings 121, also referred to as therapy parameters, that are input to the neuromodulation device by, or stored in, the clinical settings controller 302. The patient may subsequently control the device 710 to deliver the therapy according to the determined program using the remote controller 720 as described above. In one implementation, the remote controller 720 may control the target ECAP amplitude for the CLNS system 300 via the input to the target ECAP controller 304. The determined program may also, or alternatively, be loaded into the CPA for validation and modification.

VR/AR Assisted Programming System

Figure 8:
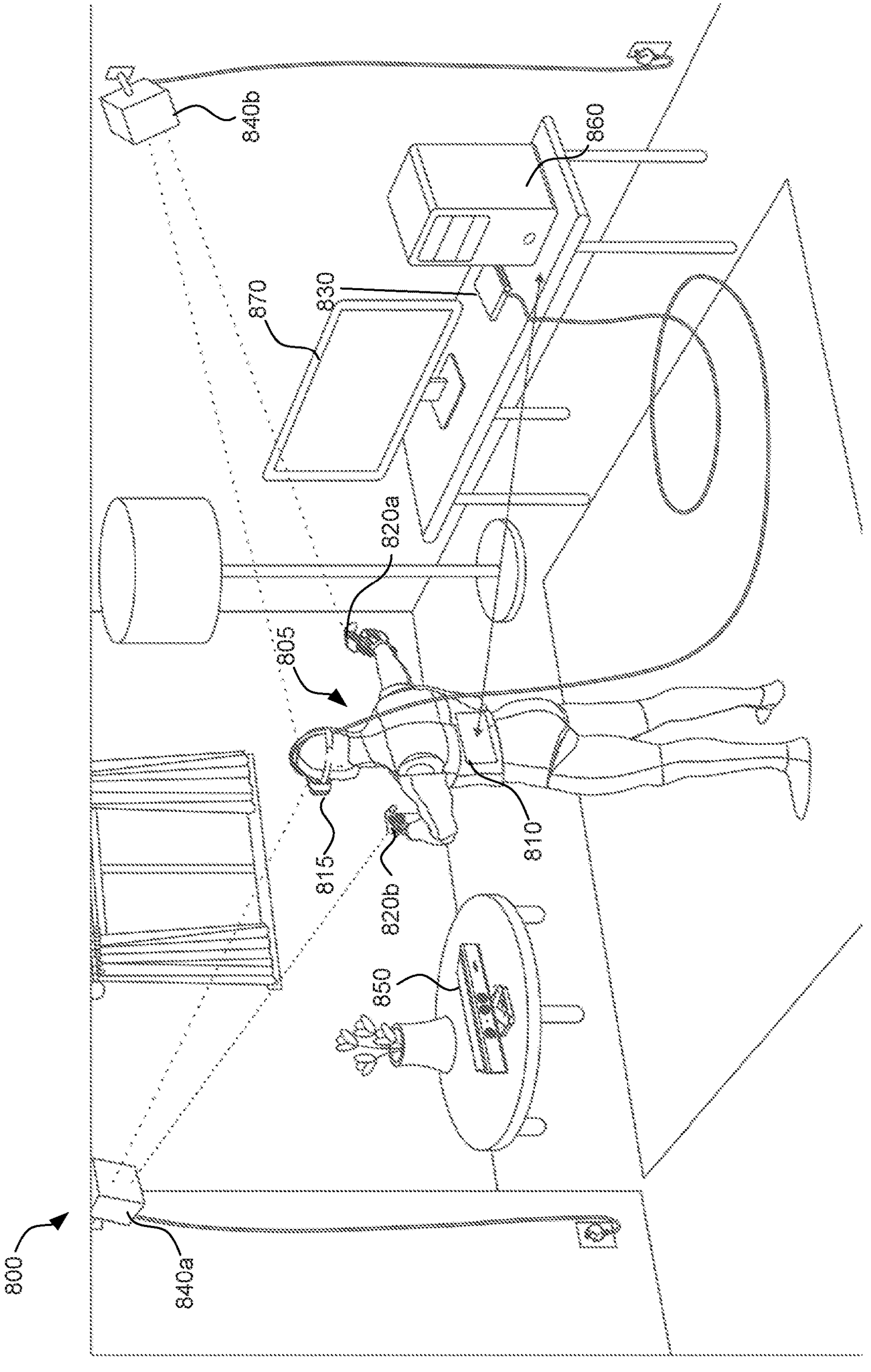
FIG. 8 is an illustration of a Programming System assisted by Virtual Reality or Augmented Reality (VR/AR) according to one aspect of the present technology.

FIG. 8 is an illustration of a Programming System 800 assisted by Virtual Reality or Augmented Reality (VR/AR)

according to one aspect of the present technology. The VR/AR-assisted programming system (APS) 800 is being operated by a patient 805 in order to program a neuromodulation device 810 that has been implanted in the patient 805 as described above. The neuromodulation device 810 may be implemented as the device 710 of FIG. 7. The neuromodulation device 810 is in communication with a clinical interface (CI) 860. The CI 860 may be implemented as the CI 740 illustrated in FIG. 7, with an integrated display. Alternatively, the CI 860 may be implemented as a computing device with a separate display 870, as illustrated in FIG. 8. The CI 860 may render images associated with the programming of the device 810 on its own integrated display or on a separate display 870 for the benefit of a third-party user (not shown) of the CI 860.

The patient 805 is wearing a headset 815. The headset 815 is principally a display device configured to display images in front of the eyes of the patient 805. In some implementations, the headset 815 is configured to display separate stereoscopic images to each eye of the patient 805 to give the patient 805 the illusion of a virtual three-dimensional (3D) environment containing virtual 3D objects. The headset 815 is in communication with a VR/AR computing device 830 from which it receives instructions as to what images to display to the eyes of the patient 805. The communication may be wired, as illustrated in FIG. 8, or wireless, making use of a short-range wireless protocol, such as Bluetooth or Zigbee.

The VR/AR-assisted programming system (APS) 800 may also comprise an additional headset (not shown) that may be worn by a clinician (not shown) assisting the patient 805 in the programming. The additional headset may replicate the view that is shown to the patient 805 by the headset 815 so that the clinician may assist the patient 805 more easily. Alternatively, the additional headset may display a view of the same virtual environment as the patient 805, in the same way as the headset 815, except from a viewpoint that is unique to the assisting clinician.

Virtual Reality (VR) and Augmented Reality (AR) are related terms that differ only in degree of immersivity, in that VR systems are generally more immersive than AR systems. VR systems immerse the user in a fully-rendered virtual environment containing no elements of actual reality perceivable by the user. AR systems, by contrast, meld virtual objects into a view of the actual environment around the patient. For AR systems, therefore, the headset 815 is configured with some degree of transparency to allow the patient 805 to view the actual environment. The headset 815 for VR systems, by contrast, is sufficiently opaque to substantially prevent the patient 805 from viewing the actual environment around the patient.

Room sensors 840*a* and 840*b* are configured to track the position and orientation of the headset 815. As the patient 805 moves his or her head, the headset 815 moves along with the head, and this movement of the headset 815 is tracked by the room sensors 840*a* and 840*b*. The room sensors 840*a* and 840*b* are in communication with the VR/AR computing device 830, which receives information representing the position and orientation of the headset 815 from the room sensors 840*a* and 840*b* from time to time. As the position and orientation of the headset 815 changes, the VR/AR computing device 830 alters the images transmitted to the headset 815 to simulate the effect of those changes on the patient's view of the virtual objects or environment being rendered. The effect is that the patient 805 perceives changes to their view of the virtual objects or environment that are consistent with the manner in which they have moved their head, just as a person's view of their actual environment changes as they move their head. This dynamic rendering dramatically increases the immersivity of the VR/AR system.

The patient 805 may hold one or more handheld controllers, in FIG. 8 illustrated as 820*a* and 820*b*. The handheld controllers 820*a* and 820*b* are configured so as to be detectable and trackable by the room sensors 840*a* and 840*b*. The room sensors 840*a* and 840*b* are configured to track the respective positions of the handheld controllers 820*a* and 820*b*. Information representing the positions and motions of the handheld controllers 820*a* and 820*b* is transmitted to the VR/AR computing device 830 by the room sensors 840*a* and 840*b*. The VR/AR computing device 830 may alter the images transmitted to the headset 815 based on the motion of the handheld controllers 820*a* and 820*b*. In particular, the handheld controllers 820*a* and 820*b* may be rendered as virtual objects whose positions in the virtual environment correspond to the positions of the handheld controllers 820*a* and 820*b* in the actual environment. This allows the patient 805 to manipulate other virtual objects by means of the handheld controllers 820*a* and 820*b*. The VR/AR computing device 830 interprets changes in the position of a handheld controller 820*a* or 820*b* as gestures carried out in order to manipulate a virtual object close to the handheld controller in predefined ways, such as touching, picking up, moving, rotating, deforming, and releasing the virtual object.

Also forming part of the VR/AR APS 800 is a posture sensor 850. The posture sensor 850 is configured to sense the position and posture of the patient's body. The posture sensor 850 is in communication with the VR/AR computing device 830, to which the posture sensor 850 transmits information representing the position and posture of the patient's body. The VR/AR computing device 830 may analyse the information to detect a dynamic activity of the patient, such as walking, as well as a static posture, such as sitting. The term "posture" in the present disclosure may therefore be read to include dynamic activity as well as static posture. The VR/AR computing device 830 may alter the images transmitted to the headset 815 based on the position and posture of the patient's body. In particular, as with the handheld controllers 820*a* and 820*b*, a representation of the patient's body 805 itself may be rendered using this information as a virtual object referred to as an "avatar". The position and posture of the patient's avatar in the virtual environment correspond to the position and posture of the patient's body in the actual environment.

In some implementations of the VR/AR APS 800 according to the present technology, the posture sensor 850 is configured to sense the position of the patient's hands in the same way that the room sensors 840*a* and 840*b* detect and track the positions of the handheld controllers 820*a* and 820*b*. This allows the patient to manipulate virtual objects without a need for the handheld controllers 820*a* and 820*b* nor sensors 840*a* and 840*b*.

In some implementations of the VR/AR APS 800 according to the present technology, the VR/AR computing device 830 is separate to, but in communication, with the CI 860. In other implementations of the VR/AR APS 800 according to the present technology, the VR/AR computing device 830 is integrated with the CI 860. In both implementations, the programming of the device 810 is carried out by the patient 805 through the CI 860 assisted by the VR/AR capability of the VR/AR computing device 830 and its ancillary devices: the headset 815, the room sensors 840*a* and 840*b*, the handheld controllers 820*a* and 820*b*, and the posture sensor 850.

According to the present technology, there are two principal functions of the VR/AR APS 800 that are assisted by the VR/AR capability: setting of therapy parameters (clinical settings); and providing feedback about the patient's condition or about sensations experienced during neural stimulation. Both of these functions may be accomplished by the performance of predefined gestures by the patient in relation to virtual objects in the virtual environment, possibly while assuming predefined postures.

According to one aspect of the present technology, the patient 805 may manipulate a virtual object to control one or more therapy parameters such as stimulus electrode configuration, stimulus intensity, stimulus frequency, and pulse width. If the device 810 is a CLNS device, the therapy parameters may also include feedback loop parameters such as controller gain and target ECAP amplitude. The manipulations of the virtual object, such as changes to its position, orientation, or shape, result in changes to corresponding parameters of the test stimuli being delivered to the patient by the implantable device 810 or the feedback loop being operated by the implantable device 810. The virtual object therefore acts as a virtual control for the multiple parameters controlling the test stimuli being delivered to the patient. The rationale for this aspect of the present technology is that a patient is potentially extremely fast at instinctively learning a transform of tactile and visual feedback into sensation (so-called sensory fusion) and so will rapidly learn how to adjust their therapy parameters to give optimal pain relief.

Figure 9:
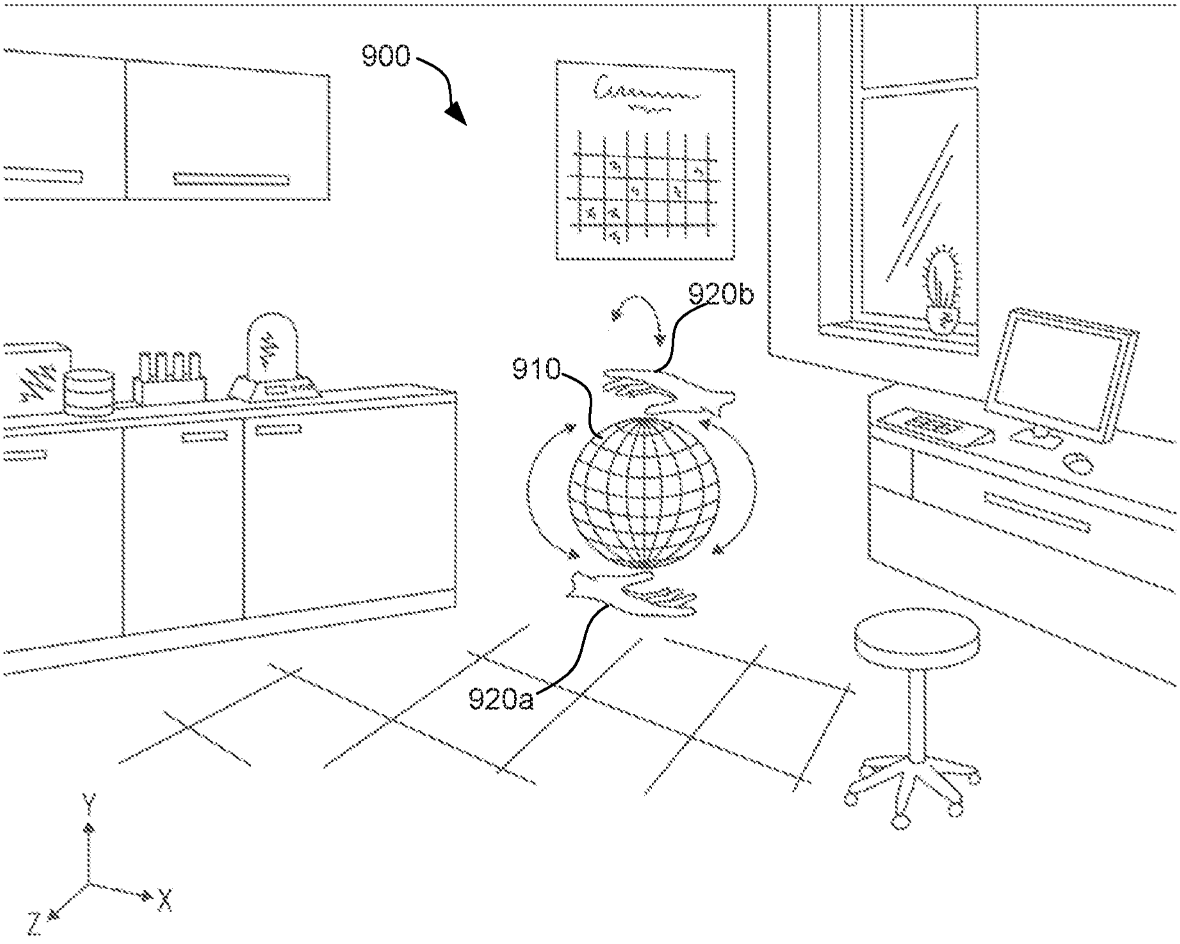
FIG. 9 is an illustration of an example of a 3D virtual environment and a 3D virtual control object that may be rendered for the patient to view via the VR/AR-assisted programming system of FIG. 8.
Figure 10:
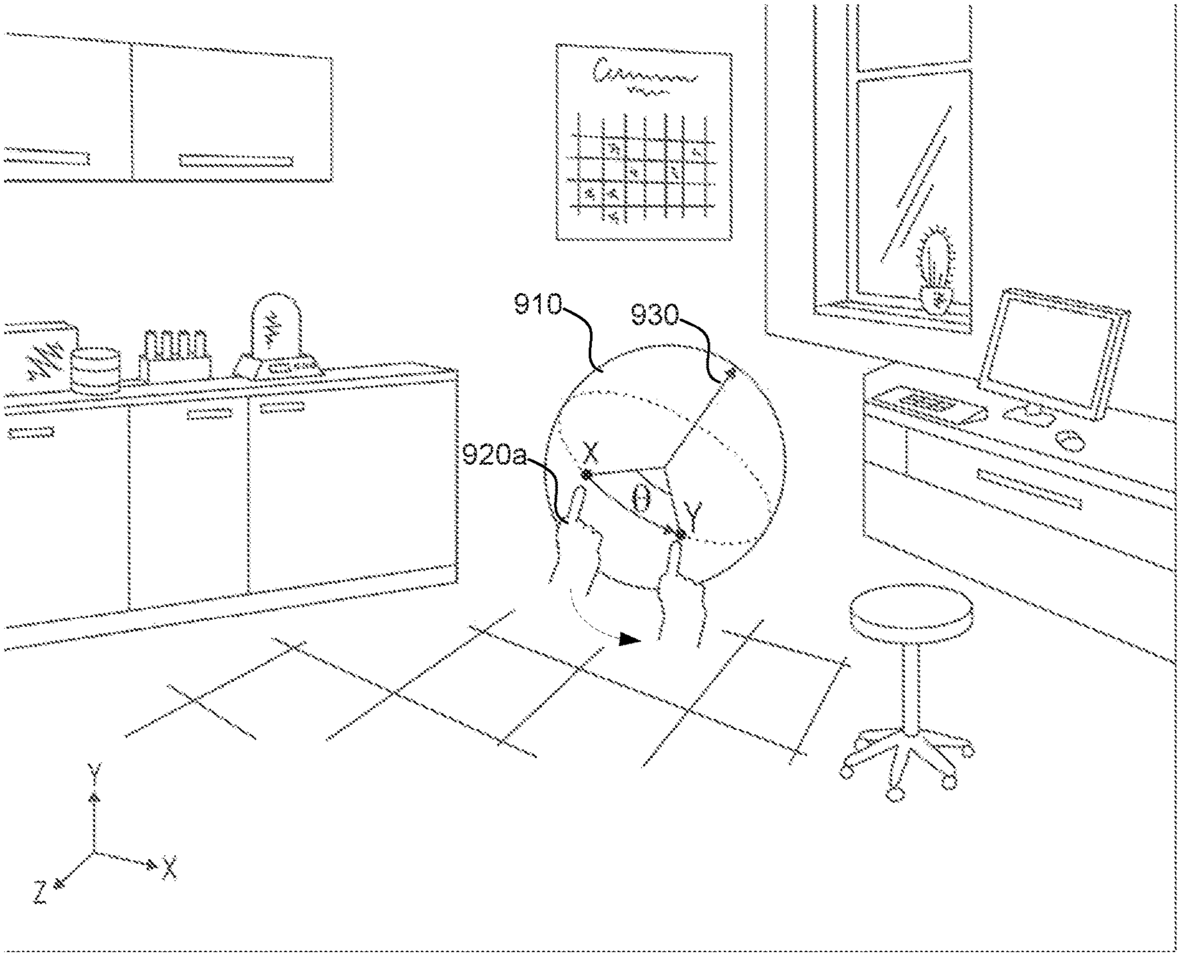
FIG. 10 illustrates the effect of a "3D rotation" manipulation of the virtual control illustrated in FIG. 9.

FIG. 9 is an illustration of an example of a 3D virtual environment 900 that may be rendered for the patient 805 to view via the headset 815. The virtual environment 900 resembles a medical laboratory, but other virtual environments may be contemplated. Rendered within the virtual environment 900 is a virtual object 910, in the shape of a sphere patterned with lines of latitude and longitude. The virtual object 910 is an example of a virtual control of the kind described above. The virtual object 910 is illustrated as close to two other rendered virtual objects represented as hands 920*a* and 920*b*. The virtual hands 920*a* and 920*b* are representations of the handheld controllers 820*a* and 820*b*, and their positions and orientations correspond to those of the handheld controllers 820*a* and 820*b* as described above. Using the handheld controllers 820*a* and 820*b*, the patient may use hand gestures to manipulate the virtual control 910 in the manner described above. The manipulations of the virtual control 910 alter the therapy parameters governing the test stimuli being delivered to the patient in real time, as described above. In one example of a manipulation, the patient may use a rotating gesture to rotate the virtual control around an arbitrary axis. FIG. 10 illustrates the effect of such a "3D rotation" gesture on the virtual control 910. The 3D rotation gesture comprises moving the virtual hand 920*a*, which is engaged with the virtual control 910, by an angle θ (approximately 45 degrees as illustrated) around an oblique axis 930 through the virtual control 910, so that the point X moves to the position Y. Any such 3D rotation may be decomposed into a rotation around a vertical axis and a separate rotation by a different angle around a horizontal axis. A 3D rotation gesture therefore comprises two independent parameter values. Each parameter of the 3D rotation gesture may be mapped to a change in a different stimulus parameter and thereby affect the sensation being experienced by the patient.

It is further contemplated that other manipulations of the virtual control 910 may affect other stimulus parameters. For example, a gesture to translate the virtual control 910 to a new 3D position within the virtual environment 900 comprises three independent parameters and therefore may be mapped to a change in each of three other stimulus parameters.

Figure 11:
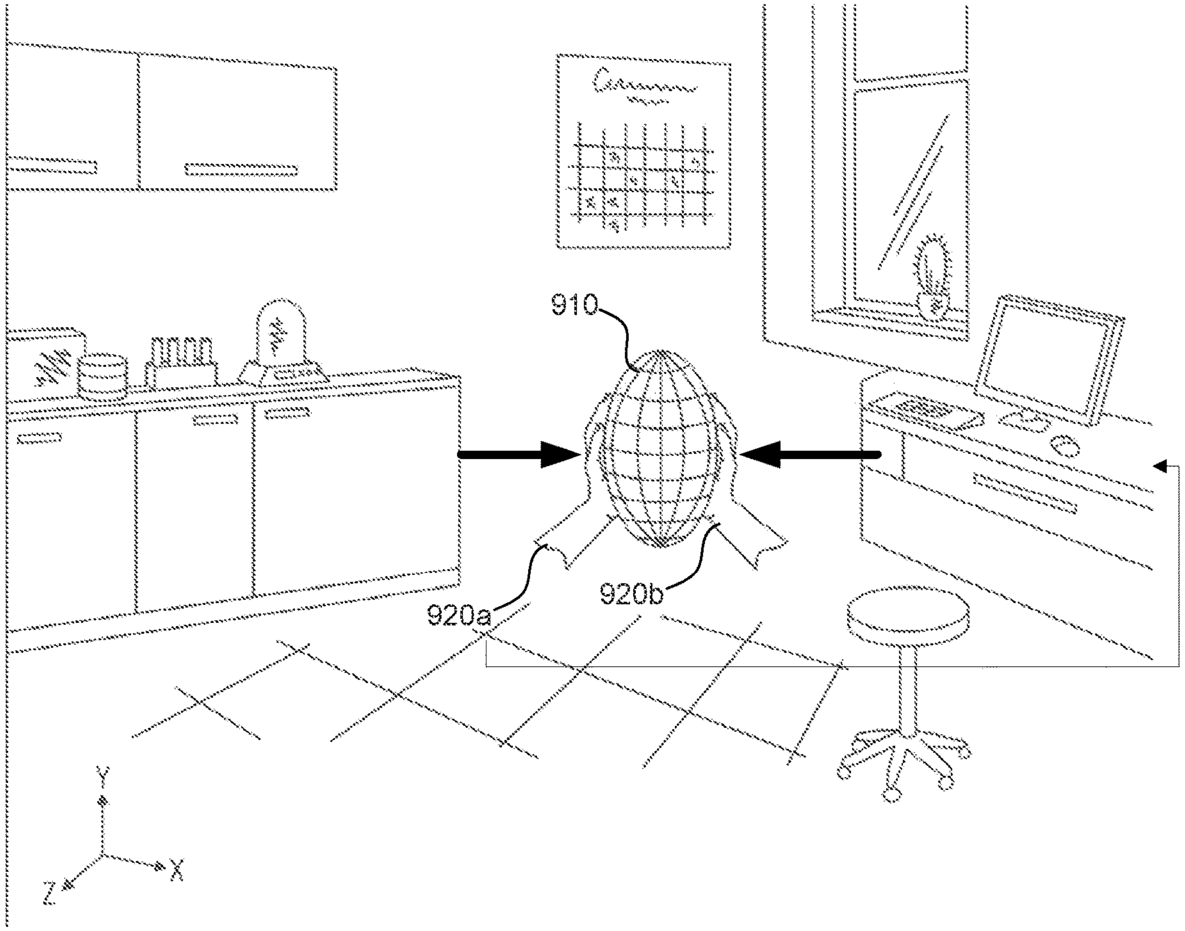
FIG. 11 illustrates the effect of a vertical distension manipulation of the virtual control illustrated in FIG. 9.

The virtual control 910 in some embodiments may not necessarily be rigid but may be deformable. In such implementations, another example of a manipulation of the virtual control 910 is to distend the virtual control along a vertical axis. FIG. 11 illustrates the result of such a manipulation, brought about by a gesture of horizontal squeezing of the virtual control 910 between the virtual hands 920*a* and 920*b*. The distention has caused the virtual control 910 to become prolate along the vertical axis. The degree of prolateness corresponds to an adjustment of a further stimulus parameter.

Figure 12:
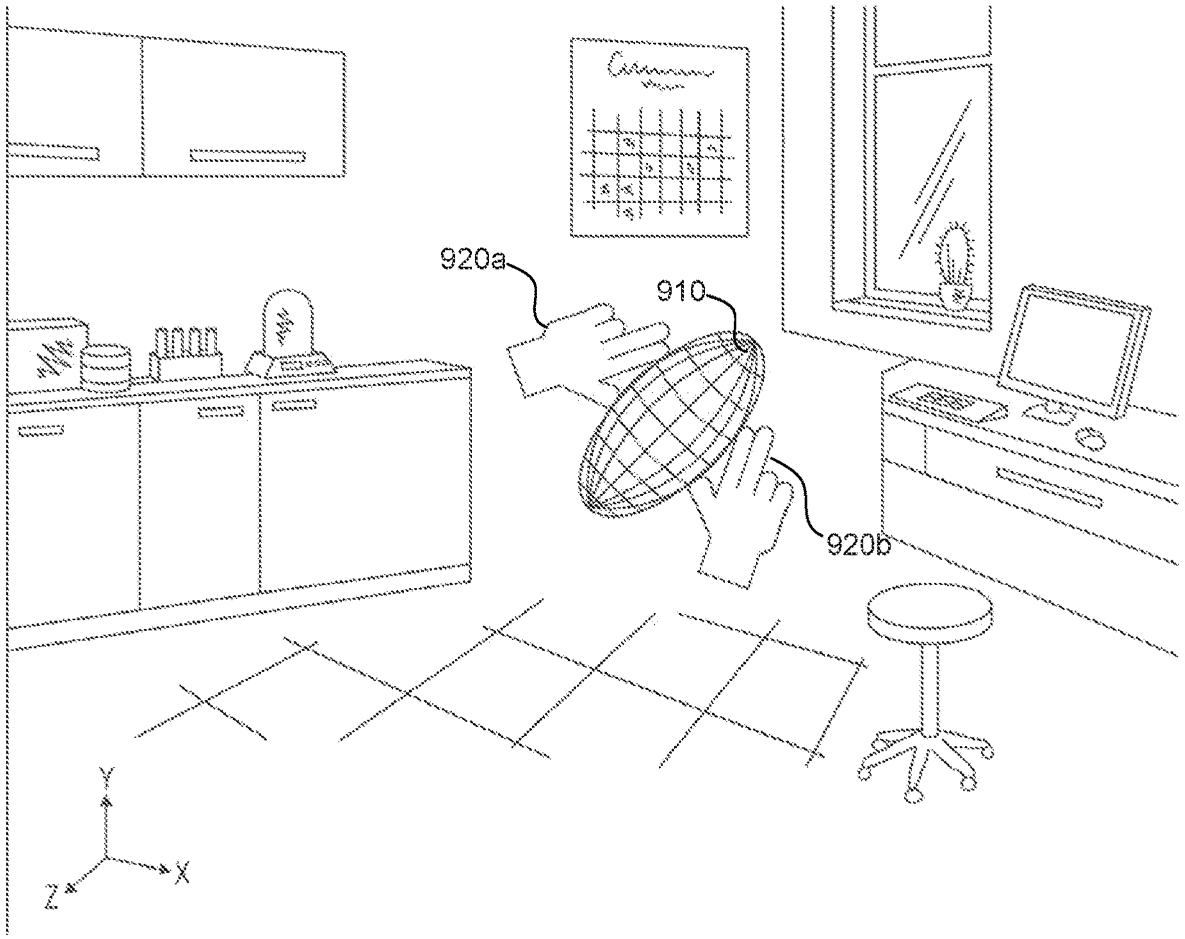
FIG. 12 illustrates the combined effect of a vertical distension as illustrated in FIG. 11 followed by a 3D rotation as illustrated in FIG. 10 on the virtual control of FIG. 9.

Manipulations of the virtual control 910 may be concatenated to achieve sequential adjustments of the corresponding stimulus parameters. In one example, FIG. 12 illustrates the combined effect on the virtual control 910 of a vertical distension as illustrated in FIG. 11 followed by a 3D rotation as illustrated in FIG. 10.

Figure 13:
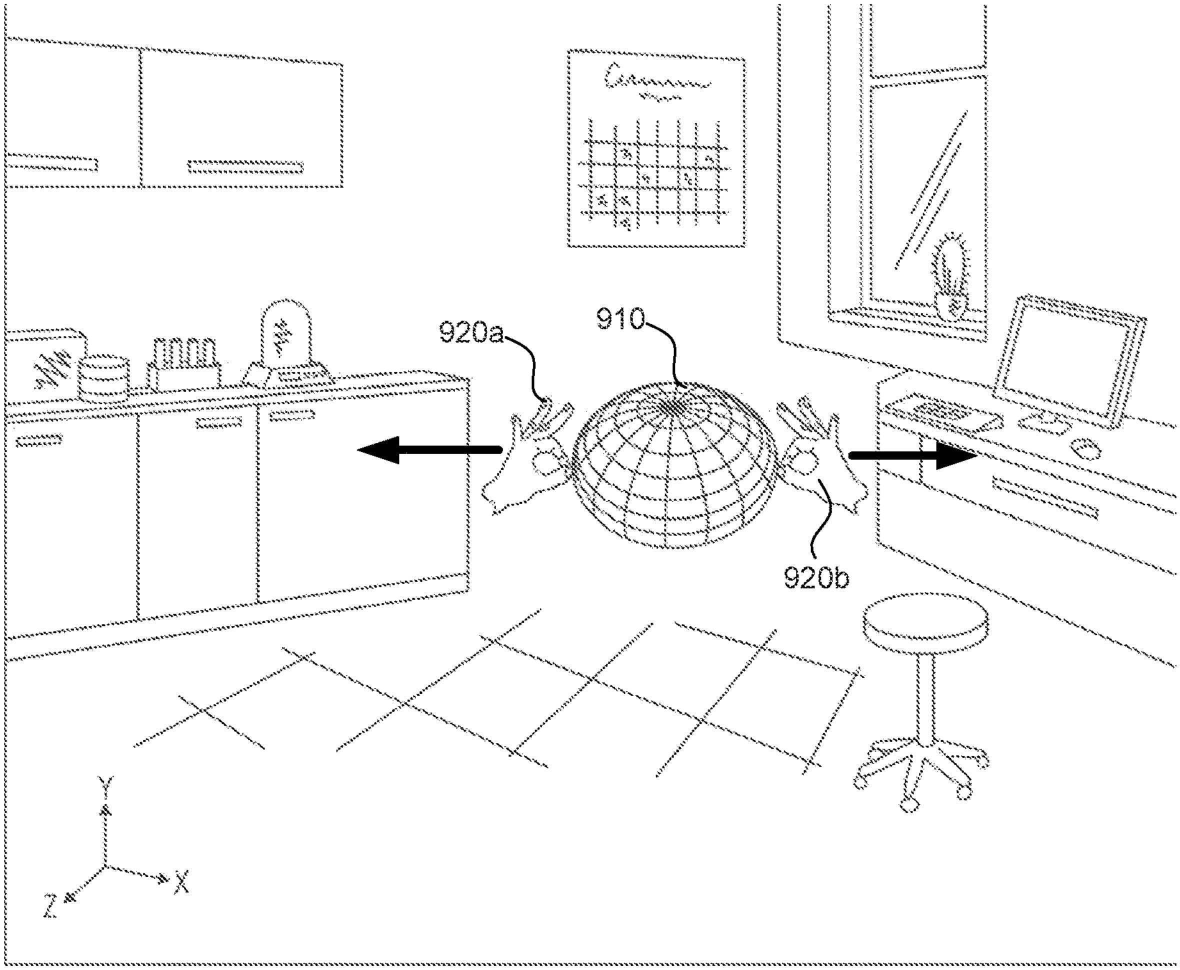
FIG. 13 illustrates the effect of a vertical compression manipulation of the virtual control illustrated in FIG. 9.

Another example of a manipulation of a deformable virtual control 910 is to compress the virtual control along a vertical axis. FIG. 13 illustrates the result of such a manipulation, brought about by a gesture of horizontal drawing out of the virtual control 910 between the virtual hands 920*a* and 920*b*. The compressing manipulation has caused the virtual control 910 to become oblate along the vertical axis. The degree of oblateness corresponds to an adjustment of a further stimulus parameter.

Figure 14:
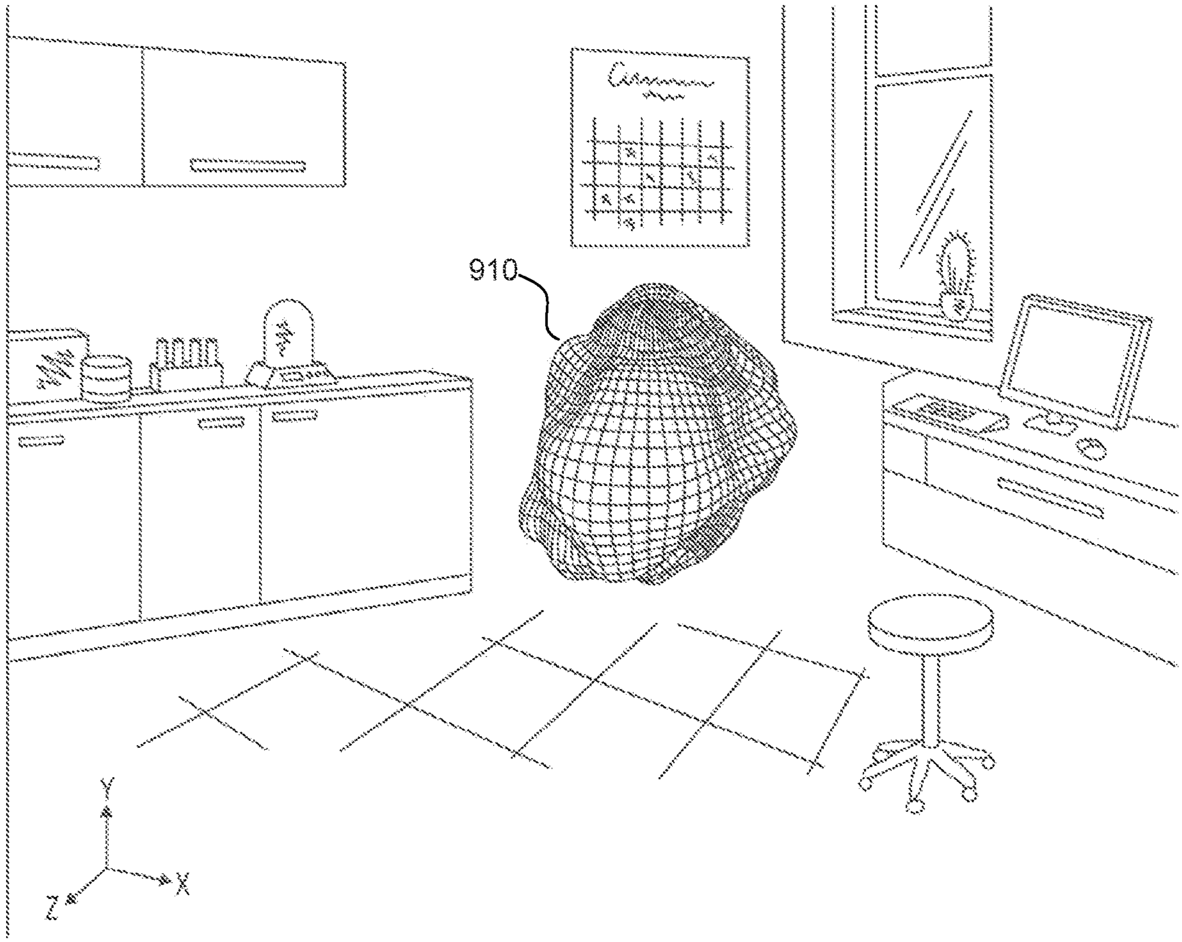
FIG. 14 illustrates the effect of many locally effective manipulations of the virtual control illustrated in FIG. 9.

The virtual control 910 may be locally as well as globally deformable. In such implementations, manipulations of the virtual control 910 may affect only local regions of the virtual control 910. Manipulations such as squashing in and drawing out of local regions of the virtual control transform the original spherical virtual object into an irregular "blob" such as illustrated in FIG. 14. In such implementations, different local regions of the virtual control may correspond to different stimulus electrode configurations. Drawing out or squashing in a local region may increase or decrease a stimulus parameter such as stimulus intensity of the corresponding stimulus electrode configuration. In this way a patient may be empowered by the present technology to deliver stimuli from multiple SECs with different parameters at each SEC in order to optimally treat their own particular combination of painful regions. This may be combined with global manipulations of the virtual control, such as the rotations, translations, and deformations previously described, that uniformly affect the corresponding parameters of all SECs.

In implementations according to this aspect, the CI 860 may set values for one or more therapy parameters once the patient is satisfied with the pain relief resulting from a particular combination of parameters. The patient may communicate their satisfaction to the CI 860 by activating a virtual "complete" control that may be rendered to the virtual environment in similar fashion to the rendering of the virtual control 910.

Figure 15:
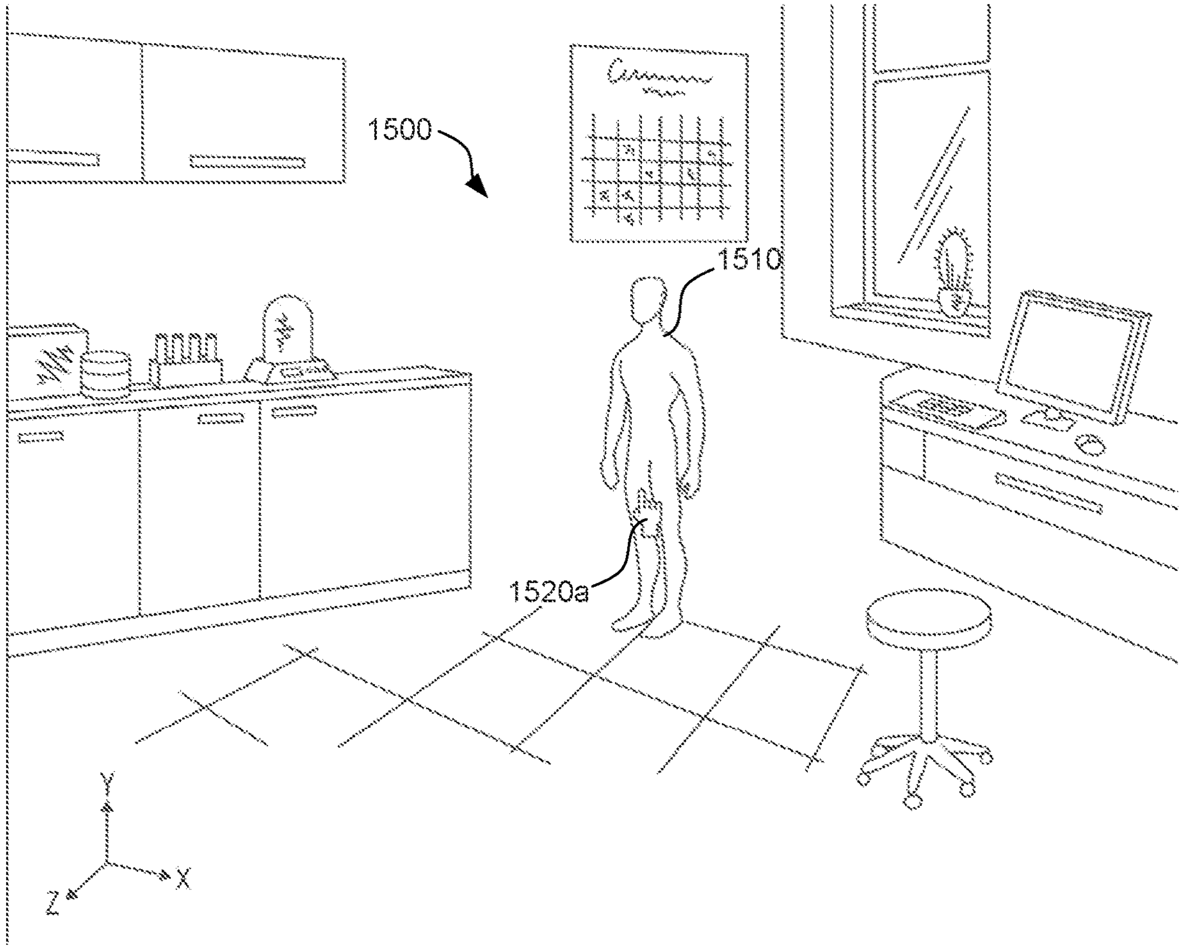
FIG. 15 is an illustration of an example of a 3D virtual environment and a 3D virtual human body that may be rendered for the patient to view via the VR/AR-assisted programming system of FIG. 8.

According to another aspect of the present technology, the patient 805 may manipulate a virtual object to provide feedback to the VR/AR APS 800 about either their own condition or the sensations being experienced in response to neural stimulation being delivered by the implantable device 810. In one such implementation, the virtual object is a human body. FIG. 15 illustrates one example of such an implementation. The virtual environment 1500 is similar to the virtual environment 900 of FIGS. 9 to 14, but contains a virtual human body 1510 instead of a virtual control. In one such implementation, while no test stimuli are being delivered, the patient "touches" the virtual body 1510 using the virtual hand 1520*a* to indicate where on their own body pain relief is desired. For example, if relief is desired in the right thigh, the patient touches the right thigh of the virtual human body 1510, as illustrated in FIG. 15. In another such implementation, while test stimuli are being delivered, the patient touches the virtual body 1510 using the virtual hand 1520*a* to indicate where on their own body sensation related to the test stimuli, such as pain relief or paraesthesia, is being felt. The virtual human body 1510 may be manipulated by hand gestures like the virtual control 910 to improve access to different parts of the virtual human body 1510. For example, FIG. 16 shows the virtual human body 1510 having been rotated "about face" so that the virtual hand 1520*a* may more easily touch the lower back region.

Figure 16:
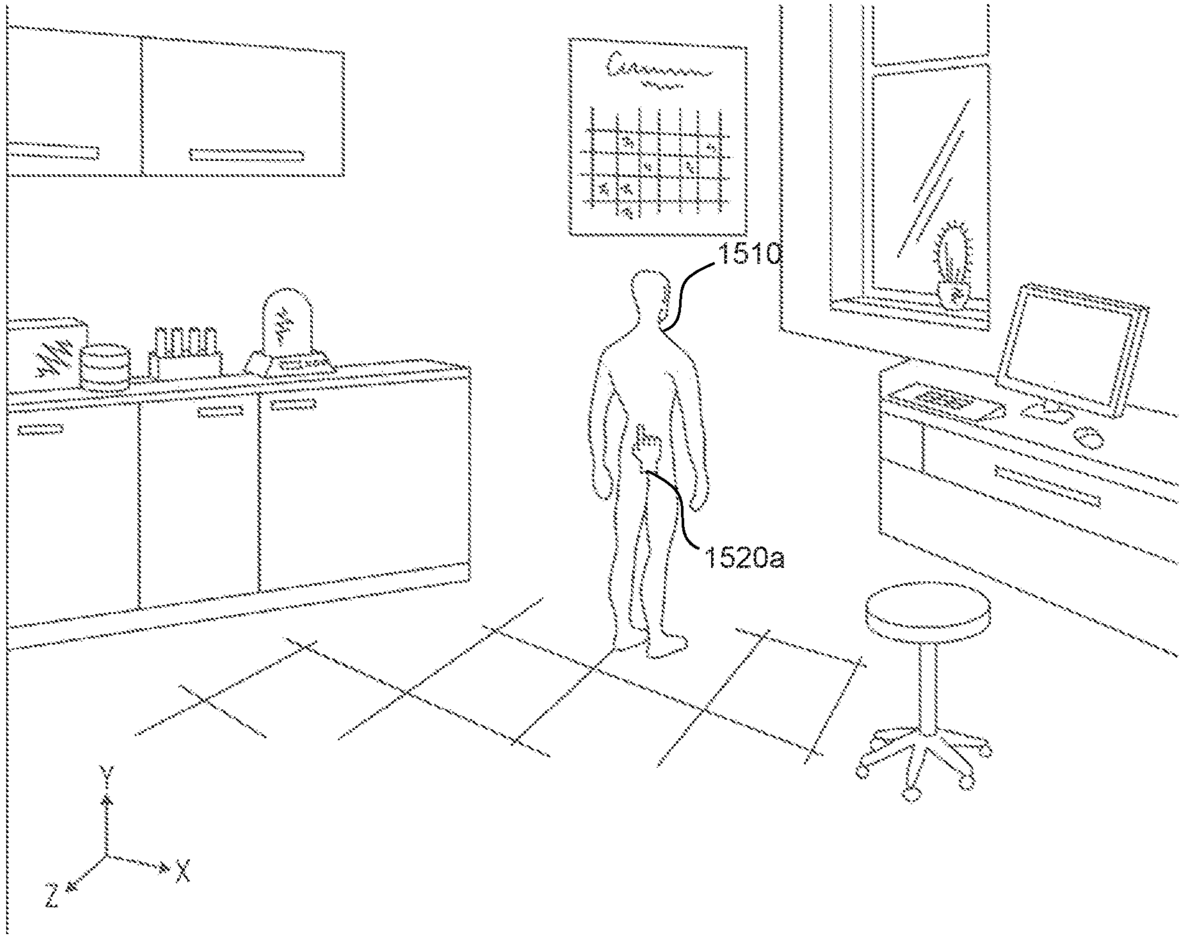
FIG. 16 illustrates the effect of an "about face" rotation of the virtual human body illustrated in FIG. 15.

In alternative implementations, the virtual human body to be touched for the above-described purposes may be the patient's own avatar rather than a separate virtual human body as illustrated in FIGS. 15 and 16.

In implementations according to this aspect, the CI 860 may determine one or more therapy parameters using the feedback about patient sensation obtained in this manner. In one example, if the location of the sensation being experienced by the patient matches the location of their painful area, the CI 860 may confirm the current SEC to form part of the therapy parameters for the patient.

According to another aspect of the present technology, the patient assumes a number of different postures in sequence, while the VR/AR APS 800 delivers test stimuli and processes the corresponding neural responses in each posture to obtain a patient characteristic. The patient characteristic may be stored in association with the posture. For example, the test stimuli may be delivered with varying stimulus intensity, and the responses used to construct an activation plot describing the patient's response to test stimuli in each posture, as described above in relation to FIG. 4*b*. International Patent Application no. PCT/AU2023/050356 by the present applicant, the contents of which are herein incorporated by reference, discloses a method of ramping stimulus intensity and analysing the corresponding neural responses to construct an activation plot in a given posture. The patient characteristics may then be estimated from the activation plot (e.g. as the key parameters of the activation plot, ECAP threshold and sensitivity). In conventional programming, the patient is asked by a clinician using the CI 740 to assume each posture in the sequence. However, according to this aspect of the present technology, the VR/AR APS 800 may be configured to detect the current posture of the patient using the posture sensor 850 as the patient moves spontaneously between postures, and to measure patient characteristics based on the responses to test stimuli delivered while the patient is in each detected posture.

In some implementations, the posture sensor 850 may be integrated with the clinical interface 860. In such implementations, the integrated posture sensor 850 may be a three-dimensional image capture apparatus. In such implementations, the clinical interface 860 may be a tablet computer or a smartphone equipped with such an integrated posture sensor.

In an alternative implementation, the VR/AR APS 800 may prompt or guide the patient to move between predefined postures, by asking the patient to interact with virtual objects that are rendered in specific places in the virtual environment corresponding to respective predefined postures. For example, the patient may be prompted to look at a virtual object rendered at the extreme left of their visual field. The patient will naturally turn their head to the left to do so, allowing test stimuli to be delivered and measurements of neural responses to be made in this posture. In another example, asking the patient to pick up a virtual object rendered on the ground at the patient's feet may prompt the patient to assume a crouching posture. Other virtual object positions corresponding to other postures may be contemplated. The implementations according to this aspect enable the programming to take place with less prescriptive involvement of the clinician.

As mentioned above, discomfort thresholds vary widely between patients, between postures for a single patient, and between stimulus electrode configurations (SECs) for a given patient in a given posture. It is difficult to know in advance where a given patient's discomfort threshold is for a given SEC in a given posture. The result is that a test stimulus of an intensity that is comfortable for one patient may provoke acute discomfort for another patient, or for the same patient in a different posture, or for the same patient in the same posture when applied at a different SEC. This means the measurement of the intensity of patients' neural responses across the therapeutic range of stimulus intensity at a particular SEC, as ideally would be performed to obtain the activation plot for that SEC, is liable to cause discomfort if carried out without either prior knowledge of the therapeutic range or real-time patient feedback.

According to another aspect of the present technology, the immersive effect of VR/AR may be utilised by the VR/AR APS 800 to modulate the attention of the patient away from their neural sensations while test stimuli are being delivered. According to this aspect, the VR/AR APS 800 may push back the actual threshold of discomfort, allowing a broader range of intensity of the test stimuli to be delivered without causing discomfort. A more accurate construction of the activation plots across different postures may thereby be obtained than are practical by conventional means. In one implementation, as the patient assumes each posture (either spontaneously or guided by the VR/AR APS 800, as described above), the VR/AR APS 800 renders soothing or engaging imagery and music to the patient while delivering the test stimuli and analysing the responses in coordination with the patient's detected postures as described above. In another such implementation, the VR/AR APS 800 engages the patient in a simple game requiring some movement and posture change to accomplish game objectives, while delivering the test stimuli and analysing the responses in coordination with the patient's detected postures as described above. One example of such a game is virtual dodge-ball. Such an implementation has the following beneficial effects:

- The attention-modulating effect that allows a broader range of intensity of the test stimuli as described above.
- The current posture of the patient may be detected by a posture sensor such as the posture sensor 850 during the spontaneous or guided movement of the patient when playing the game as described above.
- The amount of patient movement while playing the game is a good secondary indicator of therapy efficacy that can be fed back to program adjustments to converge on the most effective therapy.

According to another aspect of the present technology, the VR/AR APS 800 renders an animated virtual assistant to guide the patient 805 through a workflow of programming the device 810 with suitable therapy parameters for their particular condition and anatomy. Such a programming workflow is disclosed, for example, in International Patent Application no. PCT/AU2022/051556 by the present applicant, the contents of which are hereby incorporated by reference. The animated virtual assistant is configured to speak the guiding instructions at each stage of the workflow and to respond to any spoken queries by the patient.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

LABEL LIST

| | |
|---|---|
| stimulator | 100 |
| patient | 108 |
| electronics module | 110 |
| battery | 112 |
| telemetry module | 114 |
| controller | 116 |
| memory | 118 |
| clinical data | 120 |
| clinical settings | 121 |
| control programs | 122 |
| pulse generator | 124 |
| electrode selection module | 126 |
| measurement circuitry | 128 |
| ground | 130 |
| electrode array | 150 |
| biphasic stimulus pulse | 160 |
| neural response | 170 |
| nerve | 180 |
| transcutaneous communications channel | 190 |
| external computing device | 192 |
| system | 300 |
| clinical settings controller | 302 |
| target ECAP controller | 304 |
| box | 308 |
| box | 309 |
| controller | 310 |
| box | 311 |
| stimulator | 312 |
| element | 313 |
| measurement circuitry | 318 |
| ECAP detector | 320 |
| comparator | 324 |
| gain element | 336 |
| integrator | 338 |
| activation plot | 402 |
| ECAP threshold | 404 |
| discomfort threshold | 408 |
| perception threshold | 410 |
| therapeutic range | 412 |
| activation plot | 502 |
| activation plot | 504 |
| activation plot | 506 |
| ECAP threshold | 508 |
| ECAP threshold | 510 |
| ECAP threshold | 512 |
| ECAP target | 520 |
| ECAP | 600 |
| neuromodulation system | 700 |
| neuromodulation device | 710 |
| remote controller | 720 |
| CST | 730 |
| CI | 740 |
| charger | 750 |
| VR/AR - assisted APS | 800 |
| patient | 805 |
| device | 810 |
| headset | 815 |
| handheld controller | 820a |
| handheld controller | 820b |
| VR/AR computing device | 830 |
| room sensor | 840a |
| room sensor | 840b |
| posture sensor | 850 |
| CI | 860 |
| separate display | 870 |

-continued

LABEL LIST

| | |
|---|---|
| virtual environment | 900 |
| virtual control | 910 |
| virtual hand | 920a |
| virtual hand | 920b |
| axis | 930 |
| virtual environment | 1500 |
| virtual human body | 1510 |
| virtual hand | 1520a |

The invention claimed is:

1. A neurostimulation system comprising:

a neuromodulation device for controllably delivering neural stimuli, the neuromodulation device comprising:

a plurality of implantable electrodes;

a stimulus source configured to deliver neural stimuli via one or more of the implantable electrodes to a neural pathway of a patient; and a control unit configured to control the stimulus source to deliver each neural stimulus according to one or more stimulus parameters;

a headset configured to be worn by the patient and to display a virtual object to the patient;

one or more sensors configured to perceive a gesture of the patient; and an external computing device comprising a processor in communication with the neuromodulation device, the headset, and the one or more sensors, the processor being configured to:

instruct the control unit to control the stimulus source to deliver a neural stimulus according to the one or more stimulus parameters;

transmit the virtual object to the headset for display to the patient;

receive information indicative of a gesture of the patient from the one or more sensors; and convert the information indicative of the gesture to a manipulation of the virtual object, wherein the virtual object is a virtual control object, and the processor is further configured to:

adjust a stimulus parameter of the one or more stimulus parameters based on the manipulation of the virtual control object;

transmit the adjusted stimulus parameter to the neuromodulation device; and instruct the control unit to control the stimulus source to deliver a neural stimulus according to the adjusted stimulus parameter.

2. A neurostimulation system comprising:

a neuromodulation device for controllably delivering neural stimuli, the neuromodulation device comprising:

a plurality of implantable electrodes;

a stimulus source configured to deliver neural stimuli via one or more of the implantable electrodes to a neural pathway of a patient; and a control unit configured to control the stimulus source to deliver each neural stimulus according to one or more stimulus parameters;

a headset configured to be worn by the patient and to display a virtual object to the patient;

one or more sensors configured to perceive a gesture of the patient; and an external computing device comprising a processor in communication with the neuromodulation device, the headset, and the one or more sensors, the processor being configured to:

instruct the control unit to control the stimulus source to deliver a neural stimulus according to the one or more stimulus parameters;

transmit the virtual object to the headset for display to the patient;

receive information indicative of a gesture of the patient from the one or more sensors; and convert the information indicative of the gesture to a manipulation of the virtual object;

wherein the virtual object is a virtual human body, and the processor is further configured to:

convert the manipulation of the virtual human body to feedback about a sensation experienced by the patient in response to the neural stimuli being delivered by the stimulus source.

3. The neurostimulation system of claim 2, wherein the processor is further configured to:

determine one or more therapy parameters based on the feedback;

transmit the one or more therapy parameters to the neuromodulation device; and instruct the control unit to control the stimulus source to deliver a neural stimulus according to the one or more therapy parameters.

4. An automated method of controllably delivering a neural stimulus to a patient, the method comprising:

delivering neural stimuli to a patient according to one or more stimulus parameters;

rendering a virtual object to images for display to the patient via a headset configured to be worn by the patient and to display images of a virtual object to the patient;

receiving information indicative of a gesture of the patient via one or more sensors configured to perceive a gesture of the patient; and converting the information indicative of the gesture to a manipulation of the virtual object, wherein the virtual object is a virtual control object, the method further comprising:

adjusting a stimulus parameter of the one or more stimulus parameters based on the manipulation of the virtual control object; and delivering a neural stimulus according to the adjusted stimulus parameter.

5. An automated method of controllably delivering neural stimuli to a patient, the method comprising:

delivering neural stimuli to a patient according to one or more stimulus parameters;

rendering a virtual object to images for display to the patient via a headset configured to be worn by the patient and to display images of a virtual object to the patient;

receiving information indicative of a gesture of the patient via one or more sensors configured to perceive a gesture of the patient; and converting the information indicative of the gesture to a manipulation of the virtual object, wherein the virtual object is a virtual human body, the method further comprising:

converting the manipulation of the virtual human body to feedback about a sensation experienced by the patient in response to the neural stimuli.

6. The method of claim 5, further comprising:

determining one or more therapy parameters based on the feedback; and deliver a neural stimulus according to the one or more therapy parameters.

* * * * *